United States Patent
Meng

(10) Patent No.: US 7,371,895 B2
(45) Date of Patent: *May 13, 2008

(54) SALT FORMS OF POORLY SOLUBLE PROBUCOL ESTERS AND ETHERS

(75) Inventor: Charles Q. Meng, Alpharetta, GA (US)

(73) Assignee: AtheroGenics, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/263,821

(22) Filed: Nov. 1, 2005

(65) Prior Publication Data

US 2006/0079713 A1   Apr. 13, 2006

Related U.S. Application Data

(63) Continuation of application No. 10/619,268, filed on Jul. 14, 2003, now Pat. No. 6,960,683.

(60) Provisional application No. 60/395,573, filed on Jul. 12, 2002.

(51) Int. Cl.
C07C 321/00 (2006.01)
C07C 315/00 (2006.01)
A01N 31/08 (2006.01)

(52) U.S. Cl. .................. 562/426; 562/427; 514/732; 514/738

(58) Field of Classification Search ............... 562/512, 562/405, 426, 427; 564/463, 503; 568/700, 568/715, 716, 718, 780, 817, 816, 822, 823; 514/553, 579, 706, 724, 732, 738
See application file for complete search history.

(56) References Cited

U.S. PATENT DOCUMENTS

| | | | |
|---|---|---|---|
| 4,522,811 A | 6/1985 | Epstein et al. | |
| 4,954,514 A | 9/1990 | Kita et al. | |
| 5,155,250 A | 10/1992 | Parker et al. | |
| 5,262,439 A | 11/1993 | Parthasarathy | |
| 5,608,095 A | 3/1997 | Parker et al. | |
| 6,121,319 A * | 9/2000 | Somers | 514/548 |
| 6,147,250 A | 11/2000 | Somers | |
| 6,852,878 B2 | 2/2005 | Meng et al. | |
| 6,960,683 B2 * | 11/2005 | Meng | 562/427 |
| 2001/0029660 A1 | 10/2001 | Johnson | |
| 2001/0032014 A1 | 10/2001 | Yang et al. | |
| 2004/0204485 A1 | 10/2004 | Sikorski et al. | |
| 2005/0065121 A1 | 3/2005 | Sikorski et al. | |
| 2005/0171028 A1 | 8/2005 | Meng et al. | |
| 2005/0267187 A1 | 12/2005 | Weingarten | |
| 2006/0020038 A1 | 1/2006 | Meng et al. | |

FOREIGN PATENT DOCUMENTS

| | | |
|---|---|---|
| EP | 0348203 A1 | 12/1989 |
| EP | 0405788 A2 | 1/1991 |
| FR | 2130975 A5 | 11/1972 |
| FR | 2133024 A5 | 11/1972 |
| FR | 2134810 A5 | 12/1972 |
| FR | 2140769 A5 | 1/1973 |
| FR | 2140771 A5 | 1/1973 |
| FR | 2168137 A1 | 8/1973 |
| WO | WO 95/15760 A1 | 6/1995 |
| WO | WO 01/70757 A2 | 9/2001 |

OTHER PUBLICATIONS

Brown, L., et al., "Transdermal Delivery of Drugs," *Ann. Rev. Med.*, 39:221-229 (1988).

Kaplan, N.M. "Chapter 26: Systemic hypertension: mechanisms and diagnosis," in *Heart Disease*, 5th ed., Braunwald, E., Ed. (W.B. Saunders & Co., Philadelphia, 1997), pp. 807-823.

Meng, C.Q., et al., "Novel phenolic antioxidants as multifunctional inhibitors of inducible VCAM-1 expression for use in atherosclerosis," *Bioorg. Med. Chem. Ltrs.*, 12(18):2545-2548 (2002).

Sundell, C., et al., "AGIX-4207: A novel antioxidant and anti-inflammatory compound inhibits progression of collagen II arthritis in the rat," *FASEB Journal*, 16(4): A182 (Apr. 20-24, 2002), Annual Meeting of the Professional Research Scientists on Experimental Biology, ISSN 0892-6638.

* cited by examiner

*Primary Examiner*—Karl Puttlitz
(74) *Attorney, Agent, or Firm*—King & Spalding

(57) ABSTRACT

Organic amine salts of compounds of the formula:

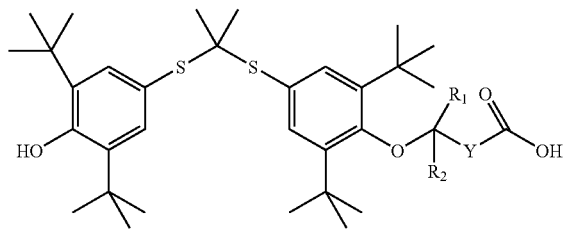

and their pharmaceutically acceptable salts, and uses in medical therapy are provided.

24 Claims, No Drawings

SALT FORMS OF POORLY SOLUBLE PROBUCOL ESTERS AND ETHERS

CROSS-REFERENCE OF THE INVENTION

This application is a continuation of U.S. application Ser. No. 10/619,268, filed Jul. 14, 2003, now U.S. Pat. No. 6,960,683, which claims priority to U.S. Provisional Patent Application No. 60/395,573, filed Jul. 12, 2002.

BACKGROUND OF THE INVENTION

Certain di- and mono-esters of probucol have been disclosed in U.S. Pat. No. 5,262,439 ('439), assigned to Atherogenics. Mono-esters and mono-ethers of probucol are also disclosed in U.S. Pat. Nos. 6,147,250 ('250) and 6,121,319 ('319), also assigned to Atherogenics. These mono-esters and mono-ethers have been shown to have significant biological activity against cardiovascular and inflammatory diseases. These compounds and others of the '250 patent are not known to be readily soluble in water. Although not a completely accurate measure of drug absorption, poor water solubility is frequently correlated to low drug absorption and bioavailability.

A series of French patents disclose that certain probucol derivatives are hypocholesterolemic and hypolipemic agents: Fr 2168137 (bis 4hydroxyphenylthioalkane esters); Fr 2140771 (tetralinyl phenoxy alkanoic esters of probucol); Fr 2140769 (benzofuryloxyalkanoic acid derivatives of probucol); Fr 2134810 (bis-(3-alkyl-5-t-alkyl-4-thiazole-5-carboxy)phenylthio)alkanes; FR 2133024 (bis-(4-nicotinoyloxyphenylthio)propanes; and Fr 2130975 (bis(4-phenoxyalkanoyloxy)phenylthio)alkanes).

U.S. Pat. No. 5,155,250 to Parker, et al. discloses that 2,6-dialkyl-4-silylphenols are antiatherosclerotic agents. The same compounds are disclosed as serum cholesterol lowering agents in PCT Publication No. WO 95/15760, published on Jun. 15, 1995. U.S. Pat. No. 5,608,095 to Parker, et al. discloses that alkylated-4-silyl-phenols inhibit the peroxidation of LDL, lower plasma cholesterol, and inhibit the expression of VCAM-1, and thus are useful in the treatment of atherosclerosis.

A series of European patent applications to Shionogi Seiyaku Kabushiki Kaisha disclose phenol esters for use in treating arteriosclerosis. European Patent Application No. 348 203 discloses phenolic thioethers which inhibit the denaturation of LDL and the incorporation of LDL by macrophages. The compounds are useful as anti-arteriosclerosis agents. Hydroxamic acid derivatives of these compounds are disclosed in European Patent Application No. 405 788 and are useful for the treatment of arteriosclerosis, ulcer, inflammation and allergy. Carbamoyl and cyano derivatives of the phenolic thioethers are disclosed in U.S. Pat. No. 4,954,514 to Kita, et al.

WO 01/70757 filed by AtheroGenics, Inc. and published on Sep. 27, 2001, describes the use of certain thioethers of the following formula, and pharmaceutically acceptable salts thereof:

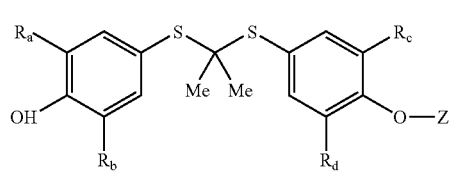

(I)

wherein
a) Ra, Rb, Rc, and Rd are independently any group that does not adversely affect the desired properties of the molecule, including hydrogen, alkyl, substituted alkyl, aryl, substituted aryl, heteroaryl, substituted heteroaryl, alkaryl, substituted alkaryl, aralkyl, or substituted aralkyl; and
b) Z is (i) a substituted or unsubstituted carbohydrate, (ii) a substituted or unsubstituted alditol, (iii) $C_{1-10}$alkyl or substituted $C_{1-10}$alkyl, terminated by sulfonic acid, (iv) $C_{1-10}$alkyl or substituted $C_{1-10}$alkyl, terminated by phosphonic acid, (v) substituted or unsubstituted $C_{1-10}$alkyl-O—C(O)—$C_{1-10}$alkyl, (vi) straight chained polyhydroxylated $C_{3-10}$ alkyl; (vii) —$(CR_2)$1-6-COOH, wherein R is independently hydrogen, halo, amino, or hydroxy, and wherein at least one of the R substituents is not hydrogen; or (viii) —$(CR_2)$1-6-X, wherein X is aryl, heteroaryl, or heterocycle, and R is independently hydrogen, halo, amino, or hydroxy.

Meng et al., discloses a series of phenolic compounds that have been discovered as potent inhibitors of TNF-α-inducible expression of vascular cell adhesion molecule-1 (VCAM-1) with concurrent antioxidant and lipid-modulating properties. The compounds disclosed have demonstrated efficacies in animal models of atherosclerosis and hyperlipidemia. (*Novel Phenolic Antioxidants As Multifunctional Inhibitors Of Inducible VCAM-1 Expression For Use In Atherosclerosis, Bioorganic & Med. Chem Ltrs.* 12(18), 2545-2548, 2002).

Sundell et al., discloses a novel metabolically stable phenolic antioxidant compound derived from probucol. ([4-[[1-[[3,5-bis(1,1-dimethylethyl)-4-hydroxypehenyl]thio]-1-methylethyl]thio]2,6-bis(1,1-dimethylethyl)phenoxy]acetic acid) inhibits TNF-α-stimulated endothelial expression of VCAM-1 and MCP-1, two redox-sensitive inflammatory genes critical for the recruitment of leukocytes to joints in rheumatoid arthritis (RA), to a greater extent than ICAM-1. (AGIX-4207: *A Novel Antioxidant And Anti-Inflammatory Compound Inhibits Progression Of Collagen II Arthritis In The Rat*, FASEB Journal Vol. 16, Nov. 4, PP. A182, Mar. 20, 2002. Apr. 20-24, 2002, Annual Meeting of the Professional Research Scientists on Experimental Biology, ISSN 0892-6638).

Given that certain probucol ester and ether derivatives are of strong commercial importance for the treatment of cardiovascular and inflammatory conditions in humans, it would be useful to increase the bioavailability and pharmacokinetics of these compounds.

It is therefore an object of the present invention to increase the bioavailability of therapeutically useful probucol esters and ethers.

It is a further object of the present invention to enhance the pharmacokinetic properties of therapeutically useful probucol esters and ethers.

BRIEF SUMMARY OF THE INVENTION

It has been discovered that the bioavailability or phamacokinetics of therapeutically useful probucol esters and ethers can be enhanced by delivering the compounds in the form of the salt of an organic amine. The invention thus includes a compound of the formula:

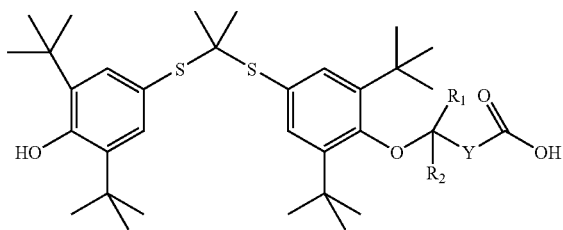

wherein $R_1$ and $R_2$ are independently hydrogen or alkyl or taken together to form a carbonyl, and Y is a $C_0$-$C_5$ alkyl (including $C_0$, $C_1$, $C_2$, $C_3$, $C_4$, and $C_5$); when $R_1$ and $R_2$ are taken together to form a carbonyl, Y is a $C_1$-$C_5$ alkyl (including $C_1$, $C_2$, $C_3$, $C_4$, and $C_5$). These new salts are surprisingly more water soluble compared to simple metal salts or the parent compounds.

In a second embodiment, the invention is represented by the organic amine salt of Formula II

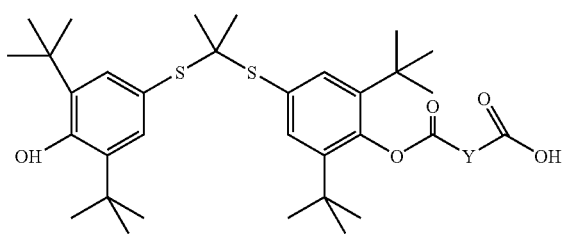

wherein:
Y is $(CH_2)_{1-5}$.

In a third embodiment, the invention is represented by the organic amine salt of Formula II, wherein Y is $(CH_2)_1$.

In a fourth embodiment, the invention is represented by the organic amine salt of Formula II, wherein Y is $(CH_2)_2$.

In a fifth embodiment, the invention is represented by the organic amine salt of Formula II, wherein Y is $(CH_2)_3$.

In a sixth embodiment, the invention is represented by the organic amine salt of Formula II wherein Y is $(CH_2)_4$.

In a seventh embodiment, the invention is represented by the organic amine salt of Formula II wherein Y is $(CH_2)_5$.

In an eighth broad embodiment, the invention is represented by the organic amine salt of Formula III

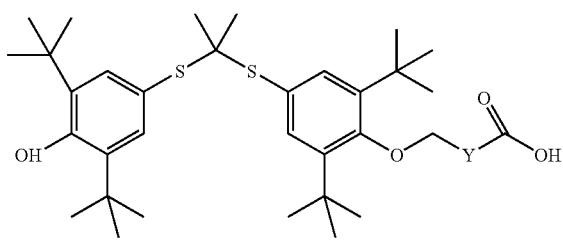

wherein:
Y is $(CH_2)_{0-5}$.

In a ninth embodiment, the invention is represented by the organic amine salt of Formula III wherein Y is $(CH_2)_0$.

In a tenth embodiment, the invention is represented by the organic amine salt of Formula III wherein Y is $(CH_2)_1$.

In an eleventh embodiment, the invention is represented by the organic amine salt of Formula III wherein Y is $(CH_2)_2$.

In a twelfth embodiment, the invention is represented by the organic amine salt of Formula III wherein Y is $(CH_2)_3$.

In a thirteenth embodiment, the invention is represented by the organic amine salt of Formula III wherein Y is $(CH_2)_4$.

In a fourteenth embodiment, the invention is represented by the organic amine salt of Formula III wherein Y is $(CH_2)_5$.

In one optional aspect of any of the embodiments of this invention, the term organic amine or other described amine counterion does not include ammonia, N,N-dibenzylethylenediamine, D-glucosamine, tetraethylammonium, ammonium, or ethylenediamine.

In a separate embodiment, the compounds of Formulas I, II or III in their non-salt form can be mixed with the organic amine forming a pharmaceutical composition. Other excipients can also be added to the composition.

The invention further constitutes pharmaceutical compositions of these salts and their usefulness in the prevention or treatment of a variety of cardiovascular, inflammatory and immune associated diseases, as disclosed in more detail in U.S. Pat. Nos. 6,147,250 and 6,121,319.

DETAILED DESCRIPTION OF THE INVENTION

In a broad first embodiment, the invention is represented by the organic amine salt of Formula I

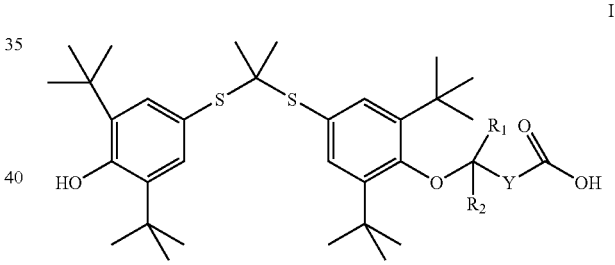

wherein:
$R_1$ and $R_2$ are independently hydrogen or alkyl or taken together to form a carbonyl; and
Y is $(CH_2)_{0-5}$; when $R_1$ and $R_2$ taken together form a carbonyl, Y is $(CH_2)_{1-5}$.

In a second embodiment, the invention is represented by the organic amine salt of Formula II

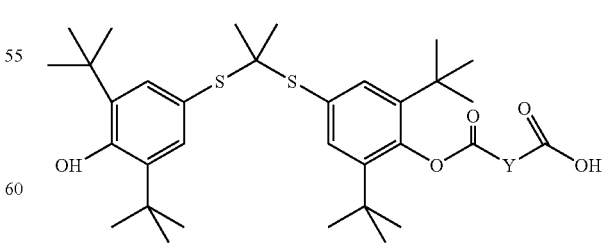

wherein:
Y is $(CH_2)_{1-5}$.

In a third embodiment, the invention is represented by the organic amine salt of Formula II, wherein Y is $(CH_2)_1$.

In a fourth embodiment, the invention is represented by the organic amine salt of Formula II, wherein Y is $(CH_2)_2$.

In a fifth embodiment, the invention is represented by the organic amine salt of Formula II, wherein Y is $(CH_2)_3$.

In a sixth embodiment, the invention is represented by the organic amine salt of Formula II wherein Y is $(CH_2)_4$.

In a seventh embodiment, the invention is represented by the organic amine salt of Formula II wherein Y is $(CH_2)_5$.

In an eighth broad embodiment, the invention is represented by the organic amine salt of Formula III

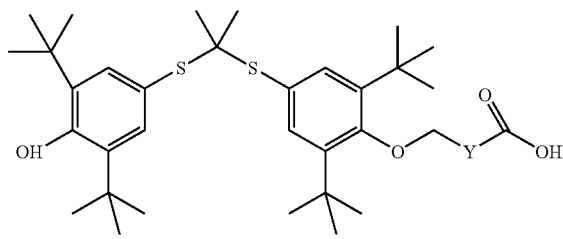

III wherein:
Y is $(CH_2)_{0-5}$.

In a ninth embodiment, the invention is represented by the organic amine salt of Formula III wherein Y is $(CH_2)_0$.

In a tenth embodiment, the invention is represented by the organic amine salt of Formula III wherein Y is $(CH_2)_1$.

In an eleventh embodiment, the invention is represented by the organic amine salt of Formula III wherein Y is $(CH_2)_2$.

In a twelfth embodiment, the invention is represented by the organic amine salt of Formula III wherein Y is $(CH_2)_3$.

In a thirteenth embodiment, the invention is represented by the organic amine salt of Formula III wherein Y is $(CH_2)_4$.

In a fourteenth embodiment, the invention is represented by the organic amine salt of Formula III wherein Y is $(CH_2)_5$.

In a separate embodiment, the compounds of Formulas I, II or III in their non-salt form can be mixed with the organic amine forming a pharmaceutical composition. Other excipients can also be added to the composition.

In another embodiment, the invention is represented by a meglumine salt of the formula IV:

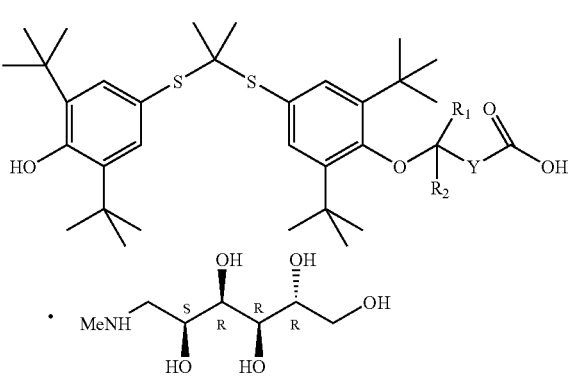

IV wherein:
$R_1$ and $R_2$ are independently hydrogen or alkyl or taken together to form a carbonyl; and
Y is $(CH_2)_{0-5}$; when $R_1$ and $R_2$ taken together form a carbonyl, Y is $(CH_2)_{1-5}$.

In another embodiment, the invention is represented by a meglumine salt of the formula V:

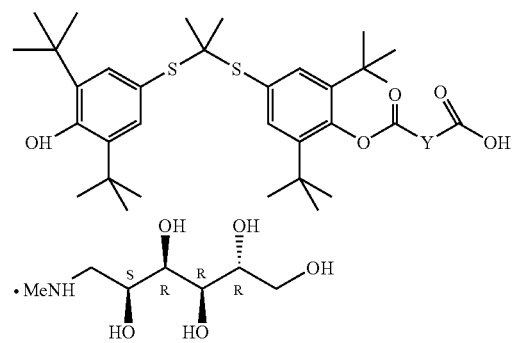

V wherein:
Y is $(CH_2)_{1-5}$.

In another embodiment, the invention is represented by the meglumine salt of the formula V wherein Y is $(CH_2)$.

In another embodiment, the invention is represented by the meglumine salt of the formula V wherein Y is $(CH_2)_2$. In another embodiment, the invention is represented by the meglumine salt of the formula V wherein Y is $(CH_2)_3$. In another embodiment, the invention is represented by the meglumine salt of the formula V wherein Y is $(CH_2)_4$.

In another embodiment, the invention is represented by the meglumine salt of the formula V wherein Y is $(CH_2)_5$.

In another embodiment, the invention is represented by the meglumine salt of the formula VI:

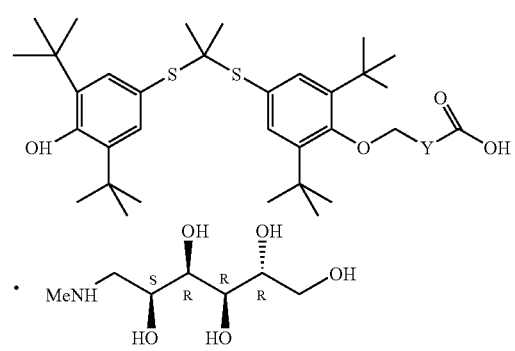

VI wherein:
Y is $(CH_2)_{0-5}$.

In another embodiment, the invention is represented by the meglumine salt of the formula VI, wherein Y is $(CH_2)_0$.

In another embodiment, the invention is represented by the meglumine salt of the formula VI, wherein Y is $(CH_2)$.

In another embodiment, the invention is represented by the meglumine salt of the formula VI, wherein Y is $(CH_2)_2$.

In another embodiment, the invention is represented by the meglumine salt of the formula VI, wherein Y is $(CH_2)_3$.

In another embodiment, the invention is represented by the meglumine salt of the formula VI, wherein Y is $(CH_2)_4$.

In another embodiment, the invention is represented by the meglumine salt of the formula VI, wherein Y is $(CH_2)_5$.

In another embodiment, the meglumine salt includes, but is not limited to, butanedioic acid, mono [4-[[1-[[3,5-bis(1, 1-dimethylethyl)-4-hydroxyphenyl]thio]-1-methylethyl]
thio]-2,6-bis(1,1-dimethylethyl)phenyl]ester, meglumine
salt; acetic acid, [4-[[1-[[3,5-bis(1,1-dimethylethyl)-4-hydroxyphenyl]thio]-1-methyl-ethyl]thio]-2,6-bis(1,1-dimethylethyl)phenoxy]-, meglumine salt; and butanoic acid, 4-[4-[[1-[[3,5-bis(1,1-dimethylethyl)-4-hydroxyphenyl]thio]-1-methyl-ethyl]thio]-2,6-bis(1,1-dimethylethyl)phenoxy]-, meglumine salt.

In another embodiment, the invention provides a method for the treatment of an inflammatory disorder, comprising administering to a host in need thereof an effective treatment amount of the salt of the compounds provided. Inflammatory disorders include, but are not limited to, arthritis, rheumatoid arthritis, osteoarthritis, asthma, multiple sclerosis, and psoriasis.

In another embodiment, the invention provides a method for the treatment of a cardiovascular disorder, comprising administering to a host in need thereof an effective treatment amount of the salt of the compounds provided. Cardiovascular diseases include, but are not limited to, atherosclerosis, post-angioplasty restenosis, coronary artery disease, small artery disease, and angina.

In another embodiment, the invention provides a method for the treatment of a disorder mediated by VCAM-1, comprising administering to a host in need thereof an effective treatment amount of the salt of the compounds.

In another embodiment, the invention provides a method for the treatment of an immune response, comprising administering to a host in need thereof an effective treatment amount of the salt of the compounds provided. Immune response include, but are not limited to, solid organ transplant rejection.

In another embodiment, the invention is an organic amine salt represented by the formula:

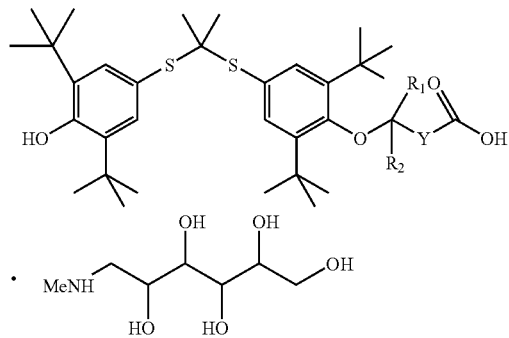

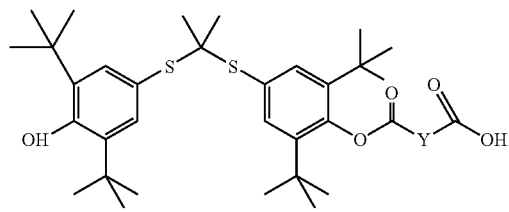

wherein:
R$_1$ and R$_2$ are independently hydrogen or alkyl or taken together to form a carbonyl; and
Y is $(CH_2)_{0-5}$; when R$_1$ and R$_2$ taken together form a carbonyl, Y is $(CH_2)_{1-5}$.

In another embodiment, the invention is represented by an organic amine salt represented by the formula:

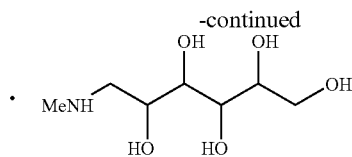

wherein:
Y is $(CH_2)_{1-5}$.

In another embodiment, the invention is represented by an organic amine salt represented by the formula:

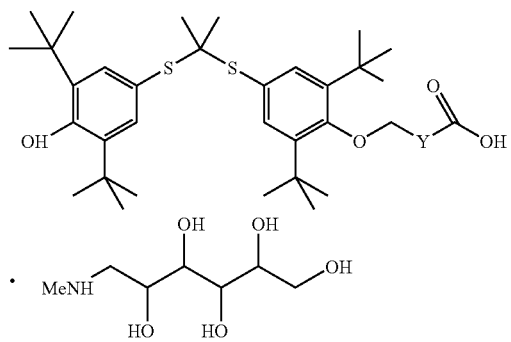

wherein:
Y is $(CH_2)_{0-5}$.

In another embodiment, the invention is represented by a compound of the formula:

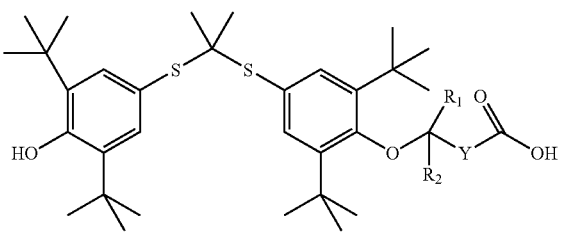

wherein:
R$_1$ and R$_2$ are independently hydrogen or alkyl or taken together to form a carbonyl; and
Y is $(CH_2)_{0-5}$; when R$_1$ and R$_2$ taken together form a carbonyl, Y is $(CH_2)_{1-5}$;
together with an organic amine, optionally in a pharmaceutically acceptable carrier.

In another embodiment, the invention is represented by a compound of the formula:

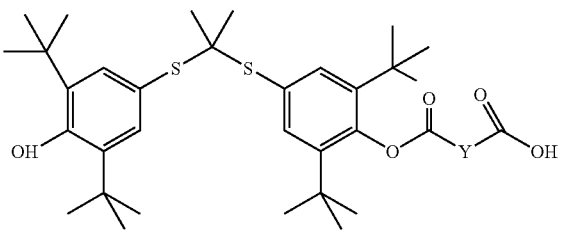

wherein:
Y is $(CH_2)_{1-5}$;
together with an organic amine, optionally in a pharmaceutically acceptable carrier.

In another embodiment, the invention is represented by a compound of the formula:

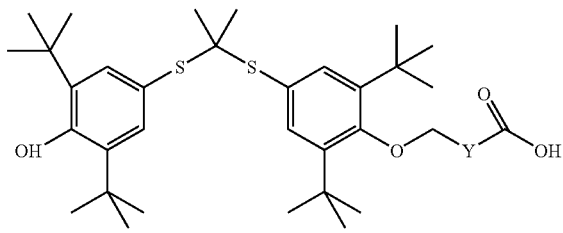

wherein:
Y is $(CH_2)_{0-5}$;
together with an organic amine, optionally in a pharmaceutically acceptable carrier.

In another embodiment, the organic amine of the invention is represented by a primary organic amine.

In another embodiment, the organic amine of the invention is represented by a secondary organic amine.

In another embodiment, the organic amine of the invention is represented by a tertiary organic amine.

In another embodiment, the organic amine of the invention is substituted with one or more hydroxy or hydroxyalkyl groups, wherein hydroxyl or hydroxyalkyl groups may be cyclic or acyclic, substituted or unsubstituted. Non-limiting examples of substituted moieties include, but are not limited to, amino sugars.

In another embodiment, the amino sugar is derived from a substituted or unsubstituted monosaccharide, disaccharide, oligosaccharide, or polysaccharide.

In another embodiment, the amino sugar is derived from an aldose or ketose.

In another embodiment, the amino sugar is derived from a pyranose or furanose.

In another embodiment, the amino sugar is derived from the group, which includes, but is not limited to, threose, ribulose, ketose, gentiobiose, aldose, aldotetrose, aldopentose, aldohexose, ketohexose, ketotetrose, ketopentose, erythrose, threose, ribose, deoxyribose, arabinose, xylose, lyxose, allose, altrose, glucose, mannose, gulose, idose, glactose, talose, erythrulose, ribulose, xylulose, psicose, fructose, sorbose, tagatose, dextrose, maltose, lactose, sucrose, cellulose, aldose, amylose, palatinose, trehalose, turanose, cellobiose, amylopectin, glucosamine, mannosamine, fucose, phamnose, glucuronate, gluconate, glucono-lactone, muramic acid, abequose, rhamnose, gluconic acid, glucuronic acid, and galactosamine.

In another embodiment, the amino sugar is derived from a (L or D)-ribose.

In another embodiment, the amino sugar is derived from a substituted or unsubstituted alditol.

In another embodiment, the substituted or unsubstituted alditol is derived from the reduction of a monosaccharide.

In another embodiment, the monosaccharide is a pyranose or furanose.

In another embodiment, the substituted and unsubstituted alditol is represented by the formula

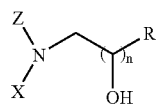

wherein:
X and Z are independently hydrogen; unsubstituted $C_{1-4}$ alkyl or substituted by one or more substituents selected from hydroxy, $C_{1-4}$ alkyl, or halogen; or taken together to form a carbocyclic ring;
R is hydrogen, $C_{1-8}$alkyl, or —$(CH_2)_{1-4}OH$; and
n is 1, 2, 3, 4 or 5.

In another embodiment, the invention includes the pharmaceutical compositions of the compounds provided, and their uses in medical therapy, and in particular, in the treatment of a cardiovascular or inflammatory disorder.

STEREOCHEMISTRY AND POLYMORPHISM

It is appreciated that compounds of the present invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms and how to determine the therapeutic activity using the standard tests described herein, or using other similar tests which are well known in the art. Examples of methods that can be used to obtain optical isomers of the compounds of the present invention include the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme iv) enzymatic asymmetric synthesis—a synthetic technique whereby at least one step of the synthesis uses an enzymatic reaction to obtain an enatiomerically pure or enriched synthetic precursor of the desired enantiomer;

v) chemical asymmetric synthesis—a synthetic technique whereby the desired enantiomer is synthesized from an achiral precursor under conditions that produce assymetry (i.e., chirality) in the product, which may be achieved using chrial catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

DEFINITIONS

The organic amines used to form the salts of the invention can be optionally substituted primary amines, secondary amines or tertiary amines, and the substituents on the amines can be straight, branched or cyclic groups, including ringed structures formed by the attachment of two or more of the amine substituents. Of particular interest are organic amines that are substituted by one or more hydroxy or hydroxyalkyl groups, including alditol and carbohydrate moieties. These hydroxy substituted organic amines can be cyclic or acyclic, both classes of which can be primary amines, secondary amines or tertiary amines. A common class of cyclic hydroxy substituted amines are the amino sugars.

Carbohydrate moieties that can comprise one or more substituents in the amine salt include those made from substituted and unsubstituted monosaccharides, disaccharides, oligosaccharides, and polysaccharides. The saccharide can be an aldose or ketose, and may comprise 3, 4, 5, 6, or 7 carbons. In one embodiment the carbohydrates are monosaccharides. In another embodiment the carbohydrates are pyranose and furanose sugars. Non limiting examples of pyranose and furanose moieties that can be part of the organic amine salt include threose, ribulose, ketose, gentiobiose, aldose, aldotetrose, aldopentose, aldohexose, ketohexose, ketotetrose, ketopentose, erythrose, threose, ribose, deoxyribose, arabinose, xylose, lyxose, allose, altrose, glucose, mannose, gulose, idose, glactose, talose, erythrulose, ribulose, xylulose, psicose, fructose, sorbose, tagatose, dextrose, maltose, lactose, sucrose, cellulose, aldose, amylose, palatinose, trehalose, turanose, cellobiose, amylopectin, glucosamine, mannosamine, fucose, phamnose, glucuronate, gluconate, glucono-lactone, muramic acid, abequose, rhamnose, gluconic acid, glucuronic acid, and galactosamine. The carbohydrate moiety can optionally be deoxygenated at any corresponding C-position, and/or substituted with one or more moieties such as hydrogen, halo (F, Cl, Br or I), halbalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, thioester, thioether, oxime, hydrazine, carbamate, phosphonic acid, phosphonate, or any other viable functional group that does not inhibit the pharmacological activity of this compound. Exemplary substituents include amine and halo, particularly fluorine. The substituent or carbohydrate can be either unprotected, or protected as necessary, as known to those skilled in the art, for example, as taught in Greene and Wuts., *Protective Groups in Organic Synthesis*, John Wiley and Sons, Third Edition, 1999. In one embodiment the monosaccharide is a furanose such as (L or D)-ribose.

The term "alkyl", as used herein, unless otherwise specified, refers to a saturated straight, branched, or cyclic, primary, secondary, or tertiary hydrocarbon of typically $C_1$ to $C_{10}$, and specifically includes methyl, $CF_3$, ethyl, propyl, isopropyl, cyclopropyl, butyl, isobutyl, secbutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups, and particularly includes halogenated alkyl groups, and even more particularly fluorinated alkyl groups. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene and Wuts., *Protective Groups in Organic Synthesis*, John Wiley and Sons, Third Edition, 1999.

The term "alkylamino" or "arylamino" refers to an amino group that has one or two alkyl or aryl substituents, respectively. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term "aryl", as used herein, and unless otherwise specified, refers to phenyl, biphenyl, or naphthyl, and preferably phenyl. The term includes both substituted and unsubstituted moieties. The aryl group can be substituted with any described moiety, including, but not limited to, one or more moieties selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene and Wuts., *Protective Groups in Organic Synthesis*, John Wiley and Sons, Third Edition, 1999.

The term "alkaryl" or "alkylaryl" refers to an alkyl group with an aryl substituent. The term aralkyl or arylalkyl refers to an aryl group with an alkyl substituent.

The term "halo", as used herein, includes chloro, bromo, iodo, and fluoro.

As used herein, the term "substantially free of" or "substantially in the absence of" refers to a compound composition that includes at least 85 or 90% by weight, preferably 95%, 98%, 99% or 100% by weight, of the designated enantiomer of that compound. In a preferred embodiment, in the methods and compounds of this invention, when stereochemistry is designated, the compounds are substantially free of their opposite enantiomers.

Similarly, the term "isolated" refers to a compound composition that includes at least 85%, 90%, 95%, 98%, 99%, or 100% by weight, of the compound, the remainder comprising other chemical species or enantiomers.

Alditol moieties refer to carbohydrates in which the aldehyde or ketone group has been reduced to an alcohol moiety. The alditols of the present invention can also be optionally substituted or deoxygenated at one or more positions. Exemplary substituents include hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, amino acid, amino acid esters and amides, phosphonyl, phosphinyl, phosphoryl, thioester, thioether, oxime, hydrazine, carbamate, phosphonic acid, and phosphonate. Particular exemplary substituents include amine and halo, particularly fluorine. The substituent or alditol can be either unprotected, or protected as necessary, as known to those skilled in the art, for example, as taught in Greene and Wuts., *Protective Groups in Organic Synthesis*, John Wiley and Sons, Third Edition, 1999. The alditol may have 3, 4, 5, 6 or 7 carbons. Examples of useful alditols are those derived from reduction of monosaccharides, including specifically those derived from the reduction of pyranose and furanose sugars.

The term "pharmaceutically acceptable salts" refer to salts or complexes that retain the desired biological activity of the compounds of the present invention and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR+A-, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Of particular interest among the acyclic organic amines is a subclass of alditols represented by the formula

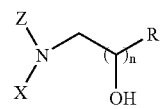

wherein X and Z are independently hydrogen or $C_{1-4}$ alkyl or may be taken together to form a carbocyclic ring, optionally substituted by one or more substituents selected from hydroxy, $C_{1-4}$ alkyl, or halogen; R is hydrogen, $C_{1-8}$alkyl, or —$CH_2)_{1-4}OH$; and n is 1, 2, 3, 4, or 5. Among these hydroxyl amines are a particular class characterized when n is 4. One specific example of a suitable organic amine is

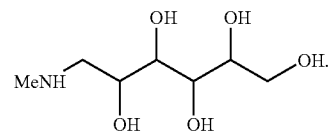

In a specific stereoconfiguration, this organic amine is referred to as "meglumine" which is also known in the art as meglumin, methylglucamin, methylglucamine, N-methylglucamine, N-MG, and 1-deoxy-1-(methylamino)-D-glucitol and has the structure of:

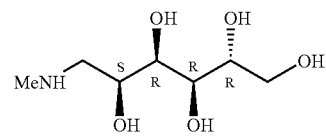

In a further embodiment of the invention, any of the above organic amine salts of the invention can be formulated as compositions, specifically pharmaceutical compositions comprising the organic amine salt and pharmaceutically acceptable carriers, diluents and/or excipients.

PHARMACEUTICAL COMPOSITIONS

While it may be possible for the compounds of the invention to be administered as the raw chemical, it is preferable to provide them as a pharmaceutical composition, for any of the disorders described herein. According to a further aspect, the present invention provides a pharmaceutical composition comprising a compound of the invention or a pharmaceutically acceptable salt or solvate thereof, together with one or more pharmaceutically acceptable carriers thereof and optionally one or more other therapeutic ingredients for any of the indications specified herein.

The formulations include those suitable for any desired administration, including but not limited to, oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the invention or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampuls and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered for example orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

The compounds of the present invention can also be administered via a catheter or stent, for example, by use of an intraluminal stent. Although stents are commonly used as part of an angioplasty procedure, intraluminal stents can be used to maintain or control any bodily luminal opening. The compound of the present invention can be used alone or as part of a composition allowing for a controlled release of the therapeutically active compound. The compounds can be coated on the stent or made a part of the stent. They may be layered so as to provide limited release of the active compound, or used in any manner known in the art as disclosed in U.S. Patent Application Nos. 20010029660 and 20010032014.

The active compound or pharmaceutically acceptable prodrugs or salts thereof can also be administered with other active materials that do not impair the desired action, or with materials that supplement the desired action, such as antibiotics, antifungals, anti-inflammatories, or antiviral compounds. The active compounds can be administered with lipid lowering agents such as probucol and nicotinic acid; platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. The compounds can also be administered in combination with nonsteroidal antiinflammatories such as ibuprofen, indomethacin, aspirin, fenoprofen, mefenamic acid, flufenamic acid, sulindac. The compound can also be administered with corticosteriods.

If administered intravenously, preferred carriers are physiological saline or phosphate buffered saline (PBS).

The active compound can also be administered through a transdermal patch. Methods for preparing transdermal patches are known to those skilled in the art. For example, see Brown, L., and Langer, R., Transdermal Delivery of Drugs, Annual Review of Medicine, 39:221-229 (1988).

In another embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylacetic acid. Methods for preparation of such formulations will be apparent to those skilled in the art. The materials can also be obtained commercially from Alza Corporation and Nova Pharmaceuticals, Inc. Liposomal suspensions may also be pharmaceutically acceptable carriers. These may be prepared according to methods known to those skilled in the art, for example, as described in U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

COMBINATION OR ALTERNATION THERAPY

The compounds of the invention, alone or as a composition, can be used alone or in combination to treat any number of diseases mediated by VCAM-1.

The compounds of the invention or their compositions, alone or in combination, can be used to treat inflammatory disorders including, but not limited to arthritis (nonlimiting examples of arthritis include rheumatoid (such as soft-tissue rheumatism and non-articular rheumatism, fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, spondyloarthropaties (ankylosing spondylitis), osteoarthritis, hyperuricemia and arthritis associated with acute gout, chronic gout and systemic lupus erythematosus), asthma, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, diabetic vasculopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, small artery disease, proliferative disorders of smooth muscle cells, and inflammatory skin diseases (such as human endothelial disorders, including but not limited to psoriasis, dermatitis, eczematous dermatitis, and Kaposi's sarcoma).

The compounds of the invention or their compositions, alone or in combination, can be used for the prevention or treatment of tissue or organ transplant rejection. Treatment and prevention of organ or tissue transplant rejection includes, but are not limited to treatment of recipients of heart, lung, combined heart-lung, liver, kidney, pancreatic, skin, spleen, small bowel, or corneal transplants. The compounds of the invention or their compositions, alone or in combination can also be used for the prevention or treatment of graft-versus-host disease, which sometimes occurs following bone marrow transplantation.

In another embodiment, the compounds of the invention or their compositions, alone or in combination, can be useful in both the primary and adjunctive medical treatment of cardiovascular disease. They can be used in the primary treatment of coronary disease states including atherosclerosis, post-angioplasty restenosis, coronary artery diseases and angina. They can be administered to treat small vessel disease that is difficult to treat by surgery or angioplasty, or other vessel disease in which surgery is not an option. They can also be used to stabilize patients prior to revascularization therapy.

The compounds of the invention or their compositions can be used to treat a variety of diseases by combining them with other known therapeutics either in combination or through alteration to increase the effectiveness against the target disease or disorder.

In combination therapy, effective dosages of two or more agents are administered together, whereas during alternation therapy an effective dosage of each agent is administered serially. The dosages will depend on absorption, inactivation and excretion rates of the drug as well as other factors known to those skilled in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The efficacy of a drug can be prolonged, augmented, or restored by administering the compound in combination or alternation with a second, and perhaps a third agent that induces a different biological pathway from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the condition.

Any method of alternation can be used that provides treatment to the patient. Nonlimiting examples of alternation patterns include 1-6 weeks of administration of an effective amount of one agent followed by 1-6 weeks of administration of an effective amount of a second agent. The alternation schedule can include periods of no treatment. Combination therapy generally includes the simultaneous administration of an effective ratio of dosages of two or more active agents.

The compounds of the invention can be administered in combination or alternation with heparin, frusemide, ranitidine, an agent that effects respiratory function (such as DNAase, or immunosuppressive agents), IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, leukotriene-$D_4$-receptor antagonists such as Accolate (zafirlukast), Ziflo (zileuton), leukotriene $C_1$ or $C_2$ antagonists and inhibitors of leukotriene synthesis such as zileuton for the treatment of asthma, or an inducible nitric oxide synthase inhibitor.

In another embodiment, the compounds of the invention are administered in combination or alternation with one or more other prophylactic agent(s). Examples of prophylactic agents that can be used in alternation or combination therapy include but are not limited to sodium cromoglycate, Intal (cromolyn sodium, Nasalcrom, Opticrom, Crolom, Ophthalmic Crolom), Tilade (nedocromil, nedocromil sodium) and ketotifen.

In another embodiment, the compounds of the invention are administered in combination or alternation with one or more other $\beta_2$-adrenergic agonist(s) ($\beta$ agonists). Examples of $\beta_2$-adrenergic agonists ($\beta$ agonists) that can be used in alternation or combination therapy include but are not limited to albuterol (salbutamol, Proventil, Ventolin), terbutaline, Maxair (pirbuterol), Serevent (salmeterol), epinephrine, metaproterenol (Alupent, Metaprel), Brethine (Bricanyl, Brethaire, terbutaline sulfate), Tornalate (bitolterol), isoprenaline, ipratropium bromide, bambuterol hydrochloride, bitolterol meslyate, broxaterol, carbuterol hydrochloride, clenbuterol hydrochloride, clorprenaline hydrochloride, efirnmoterol fumarate, ephedra (source of alkaloids), ephedrine (ephedrine hydrochloride, ephedrine sulfate), etafedrine hydrochloride, ethylnoradrenaline hydrochloride, fenoterol hydrochloride, hexoprenaline hydrochloride, isoetharine hydrochloride, isoprenaline, mabuterol, methoxyphenamine hydrochloride, methylephedrine hydrochloride, orciprenaline sulphate, phenylephrine acid tartrate, phenylpropanolamine (phenylpropanolamine polistirex, phenylpropanolamine sulphate), pirbuterol acetate, procaterol hydrochloride, protokylol hydrochloride, psuedoephedrine (psuedoephedrine polixtirex, psuedoephedrine tannate, psuedoephedrine hydrochloride, psuedoephedrine sulphate), reproterol hydrochloride, rimiterol hydrobromide, ritodrine hydrochloride, salmeterol xinafoate, terbutaline sulphate, tretoquinol hydrate and tulobuterol hydrochloride.

In another embodiment, the compounds of the invention are administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the compounds of the invention are administered in combination or alternation with one or more other antihistimine(s) ($H_1$ receptor antagonists). Examples of antihistimines ($H_1$ receptor antagonists) that can be used in alternation or combination therapy include alkylamines, ethanolamines ethylenediamines, piperazines, piperidines or phenothiazines. Some non-limiting examples of antihistimes are Chlortrimeton (Teldrin, chlorpheniramine), Atrohist (brompheniramine, Bromarest, Bromfed, Dimetane), Actidil (triprolidine), Dexchlor (Poladex, Polaramine, dexchlorpheniramine), Benadryl (diphen-hydramine), Tavist (clemastine), Dimetabs (dimenhydrinate, Dramamine, Marmine), PBZ (tripelennamine), pyrilamine, Marezine (cyclizine), Zyrtec (cetirizine), hydroxyzine, Antivert (meclizine, Bonine), Allegra (fexofenadine), Hismanal (astemizole), Claritin (loratadine), Seldane (terfenadine), Periactin (cyproheptadine), Nolamine (phenindamine, Nolahist), Phenameth (promethazine, Phenergan), Tacaryl (methdilazine) and Temaril (trimeprazine).

Alternatively, the organic amine salt of the present invention is administered in combination or alternation with xanthines and methylxanthines, such as Theo-24 (theophylline, Slo-Phylline, Uniphyllin, Slobid, Theo-Dur), Choledyl (oxitriphylline), aminophylline; anticholinergic agents (antimuscarinic agents) such as belladonna alkaloids, Atrovent (ipratropium bromide), atropine, oxitropium bromide; phosphodiesterase inhibitors such as zardaverine; calcium antagonists such as nifedipine; or potassium activators such as cromakalim for the treatment of asthma.

The compounds of the invention can also be administered in combination or alternation with apazone, amitriptyline, chymopapain, collegenase, cyclobenzaprine, diazepam, fluoxetine, pyridoxine, ademetionine, diacerein, glucosamine, hylan (hyaluronate), misoprostol, paracetamol, superoxide dismutase mimics, TNFα receptor antagonists, TNFα antibodies, P38 Kinase inhibitors, tricyclic antidepressents, cJun kinase inhibitors or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, and inducible nitric oxide sythase inhibitors.

In another embodiment, the compounds of the invention are administered in combination or alternation with one or more other non-steroidal anti-inflammatory drug(s) (NSAIDS). Examples of NSAIDS that can be used in alternation or combination therapy are carboxylic acids, propionic acids, fenamates, acetic acids, pyrazolones, oxicans, alkanones, gold compounds and others that inhibit prostaglandin synthesis, preferably by selectively inhibiting cylcooxygenase-2 (COX-2). Some nonlimiting examples of COX-2 inhibitors are Celebrex (celecoxib), Bextra (valdecoxib), Dynastat (parecoxib sodium) and Vioxx (rofacoxib). Other non-limiting examples of NSAIDS are aspirin (acetylsalicylic acid), Dolobid (diflunisal), Disalcid (salsalate, salicylsalicylate), Trisilate (choline magnesium trisalicylate), sodium salicylate, Cuprimine (penicillamine), Tolectin (tolmetin), ibuprofen (Motrin, Advil, Nuprin Rufen), Naprosyn (naproxen, Anaprox, naproxen sodium), Nalfon (fenoprofen), Orudis (ketoprofen), Ansaid (flurbiprofen), Daypro (oxaprozin), meclofenamate (meclofanamic acid, Meclomen), mefenamic acid, Indocin (indomethacin), Clinoril (sulindac), tolmetin, Voltaren (diclofenac), Lodine (etodolac), ketorolac, Butazolidin (phenylbutazone), Tandearil (oxyphenbutazone), piroxicam (Feldene), Relafen (nabumetone), Myochrysine (gold sodium thiomalate), Ridaura (auranofin), Solganal (aurothioglucose), acetaminophen, colchicine, Zyloprim (allopurinol), Benemid (probenecid), Anturane (sufinpyrizone), Plaquenil (hydroxychloroquine), Aceclofenac, Acemetacin, Acetanilide, Actarit, Alclofenac, Alminoprofen, Aloxiprin, Aluminium Aspirin, Amfenac Sodium, Amidopyrine, Aminopropylone, Ammonium Salicylate, Ampiroxicam, Amyl Salicylate, Anirolac, Aspirin, Auranofin, Aurothioglucose, Aurotioprol, Azapropazone, Bendazac (Bendazac Lysine), Benorylate, Benoxaprofen, Benzpiperylone, Benzydamine, Hydrochloride, Bornyl Salicylate, Bromfenac Sodium, Bufexamac, Bumadizone Calcium, Butibufen Sodium, Capsaicin, Carbaspirin Calcium, Carprofen, Chlorthenoxazin, Choline Magnesium Trisalicylate, Choline Salicylate, Cinmetacin, Clofexamide, Clofezone, Clometacin, Clonixin, Cloracetadol, Cymene, Diacerein, Diclofenac (Diclofenac Diethylammonium Salt, Diclofenac Potassium, Diclofenac Sodium), Diethylamine Salicylate, Diethylsalicylamide, Difenpiramide, Diflunisal, Dipyrone, Droxicam, Epirizole, Etenzamide, Etersalate, Ethyl Salicylate, Etodolac, Etofenamate, Felbinac, Fenbufen, Fenclofenac, Fenoprofen Calcium, Fentiazac, Fepradinol, Feprazone, Floctafenine, Flufenamic, Flunoxaprofen, Flurbiprofen (Flurbiprofen Sodium), Fosfosal, Furprofen, Glafenine, Glucametacin, Glycol Salicylate, Gold Keratinate, Harpagophytum Procumbens, Ibufenac, Ibuprofen, Ibuproxam, Imidazole Salicylate, Indomethacin (Indomethacin Sodium), Indoprofen, Isamifazone, Isonixin, Isoxicam, Kebuzone, Ketoprofen, Ketorolac Trometamol, Lithium Salicylate, Lonazolac Calcium, Lomoxicam, Loxoprofen Sodium, Lysine Aspirin, Magnesium Salicylate, Meclofenamae Sodium, Mefenamic Acid, Meloxicam, Methyl Butetisalicylate, Methyl Gentisate, Methyl Salicylate, Metiazinic Acid, Metifenazone, Mofebutazone, Mofezolac, Morazone Hydrochloride, Morniflurnate, Morpholine Salicylate, Nabumetone, Naproxen (Naproxen Sodium), Nifenazone, Niflumic Acid, Nimesulide, Oxametacin, Oxaprozin, Oxindanac, Oxyphenbutazone, Parsalmide, Phenybutazone, Phenyramidol Hydrochloride, Picenadol Hydrochloride, Picolamine Salicylate, Piketoprofen, Pirazolac, Piroxicam, Pirprofen, Pranoprofen, Pranosal, Proglumetacin Maleate, Proquazone, Protizinic Acid, Ramifenazone, Salacetamide, Salamidacetic Acid, Salicylamide, Salix, Salol, Salsalate, Sodium Aurothiomalate, Sodium Gentisate, Sodium Salicylate, Sodium Thiosalicylate, Sulindac, Superoxide Dismutase (Orgotein, Pegorgotein, Sudismase), Suprofen, Suxibuzone, Tenidap Sodium, Tenoxicam, Tetrydamine, Thurfyl Salicylate, Tiaprofenic, Tiaramide Hydrochloride, Tinoridine Hydrochloride, Tolfenamic Acid, Tometin Sodium, Triethanolamine Salicylate, Ufenamate, Zaltoprofen, Zidometacin and Zomepirac Sodium.

Compounds useful for combining with the compounds of the invention for the treatment of cardiovascular disease encompass a wide range of therapeutic compounds.

Ileal bile acid transporter (IBAT) inhibitors, for example, are useful in the present invention, and are disclosed in patent application no. PCT/US95/10863. More IBAT inhibitors are described in PCT/US97/04076. Still further IBAT inhibitors useful in the present invention are described in U.S. application Ser. No. 08/816,065. More IBAT inhibitor compounds useful in the present invention are described in WO 98/40375, and WO 00/38725. Additional IBAT inhibitor compounds useful in the present invention are described in U.S. application Ser. No. 08/816,065.

In another aspect, the second biologically active agent is a statin. Statins lower cholesterol levels by inhibiting of 3-hydroxy-3-methylglutaryl coenzyme A (HMG CoA) reductase, a key enzyme in the cholesterol biosynthetic pathway. The statins decrease liver cholesterol biosynthesis, which increases the production of LDL receptors thereby decreasing plasma total and LDL cholesterol (Grundy, S. M. *New Engl. J. Med.* 319, 24 (1988); Endo, A. *J. Lipid Res.* 33, 1569 (1992)). Depending on the agent and the dose used, statins may decrease plasma triglyceride levels and may increase HDLC levels. Currently the statins on the market are lovastatin (Merck), simvastatin (Merck), pravastatin (Sankyo and Squibb), fluvastatin (Sandoz), and atorvastatin (Parke-Davis/Pfizer). Any of these statins can be used in combination with the chalcones of the present invention.

MTP inhibitor compounds useful in the combinations and methods of the present invention comprise a wide variety of structures and functionalities. Some of the MTP inhibitor compounds of particular interest for use in the present invention are disclosed in WO 00/38725. Descriptions of these therapeutic compounds can be found in *Science,* 282, 23 Oct. 1998, pp. 751-754.

Cholesterol absorption antagonist compounds useful in the combinations and methods of the present invention comprise a wide variety of structures and functionalities. Some of the cholesterol absorption antagonist compounds of particular interest for use in the present invention are described in U.S. Pat. No. 5,767,115. Further cholesterol absorption antagonist compounds of particular interest for use in the present invention, and methods for making such cholesterol absorption antagonist compounds are described in U.S. Pat. No. 5,631,365.

A number of phytosterols suitable for the combination therapies of the present invention are described by Ling and Jones in "Dietary Phytosterols: A Review of Metabolism, Benefits and Side Effects," *Life Sciences,* 57 (3), 195-206 (1995). Without limitation, some phytosterols of particular use in the combination of the present invention are Clofibrate, Fenofibrate, Ciprofibrate, Bezafibrate, Gemfibrozil. The structures of the foregoing compounds can be found in WO 00/38725.

Phytosterols are also referred to generally by Nes (*Physiology and Biochemistry of Sterols*, American Oil Chemists' Society, Champaign, Ill., 1991, Table 7-2). Among the phytosterols for use in the combinations of the present invention are saturated phytosterols or stanols. Additional stanols are also described by Nes (Id.) and are useful in the combination of the present invention. In the combination of the present invention, the phytosterol preferably comprises a stanol. In one embodiment the stanol is campestanol. In another embodiment the stanol is cholestanol. In another embodiment the stanol is clionastanol. In another embodiment the stanol is coprostanol. In another embodiment the stanol is 22,23-dihydrobrassicastanol. In another embodiment the stanol is epicholestanol. In another embodiment the stanol is fucostanol. In another embodiment the stanol is stigmastanol.

Another embodiment of the present invention encompasses a therapeutic combination of a compounds of the invention and an HDLc elevating agent. In one aspect, the second HDLc elevating agent can be a CETP inhibitor. Individual CETP inhibitor compounds useful in the present invention are separately described in WO 00/38725. Other individual CETP inhibitor compounds useful in the present invention are separately described in WO 99/14174, EP818448, WO 99/15504, WO 99/14215, WO 98/04528, and WO 00/17166. Other individual CETP inhibitor compounds useful in the present invention are separately described in WO 00/18724, WO 00/18723, and WO 00/18721. Other individual CETP inhibitor compounds useful in the present invention are separately described in WO 98/35937 as well as U.S. Pat. Nos. 6,313,142, 6,310,075, 6,197,786, 6,147,090, 6,147,089, and 6,140,343.

In another combination therapy, the second biologically active agent can be a fibric acid derivative. Fibric acid derivatives useful in the combinations and methods of the present invention comprise a wide variety of structures and functionalities which have been reported and published in the art.

In another embodiment the present invention encompasses a therapeutic combination of a compound of the present invention and an antihypertensive agent. Hypertension is defined as persistently high blood pressure. For example, the compounds can be administered in combination with an ACE inhibitor, a beta andrenergic blocker, alpha andrenergic blocker, angiotensin II receptor antagonist, vasodilator and/or a diuretic.

Alternatively, the compounds or compositions of the present invention can be used alone or in combination to treat any number of diseases mediated by VCAM-1 as exemplified in the tables below.

The following list discloses these preferred statins and their preferred dosage ranges.

TABLE 1

| | Trade name | Dosage range (mg/d) | Normal dose (mg/d) | Patent Reference |
|---|---|---|---|---|
| Fungal derivatives | | | | |
| lovastatin | Mevacor | 10-80 | 20-40 | 4,231,938 |
| pravastatin | Pravachol | 10-40 | 20-40 | 4,346,227 |
| simvastatin | Zocor | 5-40 | 5-10 | 4,739,073 |
| Synthetic compound | | | | |
| Fluvastatin | Lescol | 20-80 | 20-40 | 4,739,073 |

The following list describes the chemical formula of some preferred statins:

lovastatin: [1S[1a(R), 3 alpha, 7 beta, 8 beta (2S,4S), 8a beta]]-1,2,3,7,8,8a-hexahydro-3,7-dimethyl-8-[2-(tetrahydro-4-hydroxy-6-oxo-2H-pyran-2-yl)ethyl]-1-maphtalenyl-2-methylbutanoate pravastatin sodium: 1-Naphthalene-heptanoic acid, 1,2,6,7,8a-hexahydro-beta, delta, 6-trihydroxy-2-methyl-8-(2-ethyl-1-oxybutoxy)-1-, monosodium salt [1S-[1 alpha (beta s, delta S), 2 alpha, 6 alpha, 8 beta (R), 8a alpha simvastatin: butanoic acid, 2,2-dimethyl-,1,2,3,7,8,8a-hexahydro-3,7-dimethyl-8-[2 tetrahydro-4-hydroxy-6-oxo-2H-pyran-2-yl)ethyl]-1-napthalenyl ester [1S-[1 alpha, 3 alpha, 7 beta, 8 beta, (2S,4S),-8a beta sodium fluvastatin: [R,S-(E)]-(+/−)-7-[3(4-fluorophenyl)-1-(1-methylethyl)-1H-indol-2-yl]-3,5-dihydroxy-6-heptenoic acid, monosodium salt Other statins, and references from which their description can be derived, are listed below.

TABLE 2

| STATIN | REFERENCE |
|---|---|
| Atorvastatin | U.S. Pat. No. 5,273,995 |
| Cerivastatin (Baycol) | U.S. Pat. No. 5,177,080 |
| Mevastatin | U.S. Pat. No. 3,983,140 |
| Cerivastatin | U.S. Pat. No. 5,502,199 |
| Velostatin | U.S. Pat. No. 4,448,784 |
| Compactin | U.S. Pat. No. 4,804,770 |
| Dalvastatin | EP 738510 A2 |
| Fluindostatin | EP 363934 A1 |
| Dihydorcompactin | U.S. Pat. No. 4,450,171 |

Other statins include rivastatin, SDZ-63,370 (Sandoz), CI-981 (W-L). HR-780, L-645,164, CL-274,471, alpha-, beta-, and gamma-tocotrienol, (3R,5S,6E)-9,9-bis(4-fluorophenyl)-3,5-dihydroxy-8-(1-methyl-1H-tetrazol-5-yl)-6,8-nonadienoic acid, L-arginine salt, (S)-4-[[2-[4-(4-fluorophenyl)-5-methyl-2-(1-methylethyl)-6-phenyl-3-pyridinyl]ethenyl]-hydroxyphosphinyl]-3-hydroxybutanoic acid, disodium salt, BB476, (British Biotechnology), dihydrocompactin, [4R-[4 alpha, 6 beta (E)]]-6-[2-[5-(4-fluorophenyl)-3-(1-methylethyl)-1-(2-pyridinyl)-1H-pyrazol-4-yl]ethenyl]tetrahydro-4-hydroxy-2H-pyran-2-one, and 1H-pyrrole-1-heptanoic acid, 2-(4-fluorophenyl)-beta,delta-dihydroxy-5-(1-methylethyl)-3-phenyl-4-[(phenylamino)carbonyl]calcium salt[R-(R*,R*)].

However, the invention should not be considered to be limited to the foregoing statins. Naturally occurring statins are derivatives of fungi metabolites (ML-236B/compactin/monocalin K) isolated from *Pythium ultimum, Monacus ruber, Penicillium citrinum, Penicillium brevicompactum* and *Aspergillus terreus*, though as shown above they can be prepared synthetically as well. Statin derivatives are well known in the literature and can be prepared by methods disclosed in U.S. Pat. No. 4,397,786. Other methods are cited in The Peptides: Vol. 5, Analysis, Synthesis, Biology; Academic Press NY (1983); and by Bringmann et al. in Synlett (5), pp. 253-255 (1990).

Thus, the term statin as used herein includes any naturally occurring or synthetic peptide that inhibits 3-hydroxy-3-methylglutaryl coenzyme A (HMG CoA) reductase by competing with 3-hydroxy-3-methylglutaric acid (HMG) CoA for the substrate binding site on HMG-CoA reductase. Assays for determining whether a statin acts through this biological pathway are disclosed in U.S. Pat. No. 4,231,938, column 6, and WO 84/02131 on pages 30-33.

MTP inhibitor compounds useful in the combinations and methods of the present invention comprise a wide variety of structures and functionalities. Some of the MTP inhibitor compounds of particular interest for use in the present invention are disclosed in WO 00/38725 and U.S. Pat. Nos. 6,458,851 and 6,458,850. Descriptions of these therapeutic compounds can be found in *Science*, 282, 23 Oct. 1998, pp. 751-754.

Cholesterol absorption antagonist compounds useful in the combinations and methods of the present invention comprise a wide variety of structures and functionalities. Some of the cholesterol absorption antagonist compounds of particular interest for use in the present invention are described in U.S. Pat. No. 5,767,115. Further cholesterol absorption antagonist compounds of particular interest for use in the present invention, and methods for making such cholesterol absorption antagonist compounds are described in U.S. Pat. No. 5,631,365.

A number of phytosterols suitable for the combination therapies of the present invention are described by Ling and Jones in "Dietary Phytosterols: A Review of Metabolism, Benefits and Side Effects," *Life Sciences,* 57 (3), 195-206 (1995). Without limitation, some phytosterols of particular use in the combination of the present invention are Clofibrate, Fenofibrate, Ciprofibrate, Bezafibrate, Gemfibrozil. The structures of the foregoing compounds can be found in WO 00/38725.

Phytosterols are also referred to generally by Nes (*Physiology and Biochemistry of Sterols*, American Oil Chemists' Society, Champaign, Ill., 1991, Table 7-2). Especially preferred among the phytosterols for use in the combinations of the present invention are saturated phytosterols or stanols. Additional stanols are also described by Nes (Id.) and are useful in the combination of the present invention. In the combination of the present invention, the phytosterol preferably comprises a stanol. In one preferred embodiment the stanol is campestanol. In another preferred embodiment the stanol is cholestanol. In another preferred embodiment the stanol is clionastanol. In another preferred embodiment the stanol is coprostanol. In another preferred embodiment the stanol is 22,23-dihydrobrassicastanol. In another embodiment the stanol is epicholestanol. In another preferred embodiment the stanol is fucostanol. In another preferred embodiment the stanol is stigmastanol.

In another embodiment the present invention encompasses a therapeutic combination of a compound of the present invention and another HDLc elevating agent. In one aspect, the second HDLC elevating agent can be a CETP inhibitor. Individual CETP inhibitor compounds useful in the present invention are separately described in WO 00/38725. Other individual CETP inhibitor compounds useful in the present invention are separately described in WO 99/14174, EP818448, WO 99/15504, WO 99/14215, WO 98/04528, WO 00/17166 and U.S. Pat. Nos. 6,462,091, 6,458,852, 6,458,850, 6,458,803, and 6,458,849. Other individual CETP inhibitor compounds useful in the present invention are separately described in WO 00/18724, WO 00/18723, and WO 00/18721. Other individual CETP inhibitor compounds useful in the present invention are separately described in WO 98/35937. Particular CETP inhibitors suitable for use in combination with the invention are described in *The Discovery of New Cholesteryl Ester Transfer Protein Inhibitors* (Sikorski et al., Curr. Opin. Drug Disc. & Dev., 4(5):602-613 (2001)).

In another aspect, the second HDLc elevating agent can be a fibric acid derivative. Fibric acid derivatives useful in the combinations and methods of the present invention comprise a wide variety of structures and functionalities. Particular fibric acid derivatives for the present invention are described in Table 3. The therapeutic compounds of Table 3 can be used in the present invention in a variety of forms, including acid form, salt form, racemates, enantiomers, zwitterions, and tautomers.

TABLE 3

| Common Name | CAS Registry Number | U.S. Patent Reference for Compound Per Se |
|---|---|---|
| Clofibrate | 637-07-0 | 3,262,850 |
| Fenofibrate | 49562-28-9 | 4,058,552 |
| Ciprofibrate | 52214-84-3 | 3,948,973 |
| Bezafibrate | 41859-67-0 | 3,781,328 |
| Gemfibrozil | 25182-30-1 | 3,674,836 |

In another embodiment the present invention encompasses a therapeutic combination of a compound of the present invention and an antihypertensive agent. Hypertension is defined as persistent high blood pressure. Generally, adults are classified as being hypertensive when systolic blood pressure is persistently above 140 mmHg or when diastolic blood pressure is above 90 mmHg. Long-term risks for cardiovascular mortality increase in a direct relationship with persistent blood pressure. (E. Braunwald, *Heart Disease,* 5th ed., W. B. Saunders & Co., Philadelphia, 1997, pp. 807-823.) Blood pressure is a function of cardiac output and peripheral resistance of the vascular system and can be represented by the following equation:

$$BP \text{ is } CO \times PR$$

wherein BP is blood pressure, CO is cardiac output, and PR is peripheral resistance. (Id., p. 816.) Factors affecting peripheral resistance include obesity and/or functional constriction. Factors affecting cardiac output include venous constriction. Functional constriction of the blood vessels can be caused y a variety of factors including thickening of blood vessel walls resulting in diminishment of the inside diameter of the vessels. Another factor which affects systolic blood pressure is rigidity of the aorta (Id., p. 811.)

Hypertension and atherosclerosis or other hyperlipidemic conditions often coexist in a patient. It is possible that certain hyperlipidemic conditions such as atherosclerosis can have a direct or indirect affect on hypertension. For example, atherosclerosis frequently results in diminishment of the inside diameter of blood vessels. Furthermore, atherosclerosis frequently results in increased rigidity of blood vessels, including the aorta. Both diminished inside diameter of blood vessels and rigidity of blood vessels are factors which contribute to hypertension.

Myocardial infarction is the necrosis of heart muscle cells resulting from oxygen deprivation and is usually cause by an obstruction of the supply of blood to the affected tissue. For example, hyperlipidemia or hypercholesterolemia can cause the formation of atherosclerotic plaques, which can cause obstruction of blood flow and thereby cause myocardial infarction. (Id., pp. 1185-1187.) Another major risk factor for myocardial infarction is hypertension. (Id., p. 815.) In other words, hypertension and hyperlipidemic conditions such as atherosclerosis or hypercholesterolemia work in concert to cause myocardial infarction.

Coronary heart disease is another disease, which is caused or aggravated by multiple factors including hyperlipidemic conditions and hypertension. Control of both hyperlipidemic conditions and hypertension are important to control symptoms or disease progression of coronary heart disease.

Angina pectoris is acute chest pain, which is caused by decreased blood supply to the heart. Decreased blood supply to the heart is known as myocardial ischemia. Angina pectoris can be the result of, for example, stenosis of the aorta, pulmonary stenosis and ventricular hypertrophy. Some antihypertensive agents, for example amlodipine, control angina pectoris by reducing peripheral resistance.

Some antihypertensive agents useful in the present invention are shown in Table 4, without limitation. A wide variety of chemical structures are useful as antihypertensive agents in the combinations of the present invention and the agents can operate by a variety of mechanisms. For example, useful antihypertensive agents can include, without limitation, an adrenergic blocker, a mixed alpha/beta adrenergic blocker, an alpha adrenergic blocker, a beta adrenergic blocker, an adrenergic stimulant, an angiotensin converting enzyme (ACE) inhibitor, an angiotensin II receptor antagonist, a calcium channel blocker, a diuretic, or a vasodilator. Additional hypertensive agents useful in the present invention are described by R. Scott in U.S. patent application Ser. No. 60/057,276 (priority document for PCT Patent Application No. WO 99/11260).

TABLE 4

| Antihypertensive Classification | Compound Name | Typical Dosage |
|---|---|---|
| adrenergic blocker | Phenoxybenzamine | 1-250 mg/day |
| adrenergic blocker | Guanadrel | 5-60 mg/day |
| adrenergic blocker | Guanethidine | |
| adrenergic blocker | Reserpine | |
| adrenergic blocker | Terazosin | 0.1-60 mg/day |
| adrenergic blocker | Prazosin | 0.5-75 mg/day |
| adrenergic blocker | Polythiazide | 0.25-10 mg/day |
| adrenergic stimulant | Methyldopa | 100-4000 mg/day |
| adrenergic stimulant | Methyldopate | 100-4000 mg/day |
| adrenergic stimulant | Clonidine | 0.1-2.5 mg/day |
| adrenergic stimulant | Chlorthalidone | 10-50 mg/day |
| adrenergic blocker | Guanfacine | 0.25-5 mg/day |
| adrenergic stimulant | Guanabenz | 2-40 mg/day |
| adrenergic stimulant | Trimethaphan | |
| alpha/beta adrenergic blocker | Carvedilol | 6-25 mg bid |
| alpha/beta adrenergic blocker | Labetalol | 10-500 mg/day |
| beta adrenergic blocker | Propranolol | 10-1000 mg/day |
| beta adrenergic blocker | Metoprolol | 10-500 mg/day |
| alpha adrenergic blocker | Doxazosin | 1-16 mg/day |
| alpha adrenergic blocker | Phentolamine | |
| angiotensin converting enzyme inhibitor | Quinapril | 1-250 mg/day |
| angiotensin converting enzyme inhibitor | perindopril erbumine | 1-25 mg/day |
| angiotensin converting enzyme inhibitor | Ramipril | 0.25-20 mg/day |
| angiotensin converting enzyme inhibitor | Captopril | 6-50 mg bid or tid |
| angiotensin converting enzyme inhibitor | Trandolapril | 0.25-25 mg/day |
| angiotensin converting enzyme inhibitor | Fosinopril | 2-80 mg/day |
| angiotensin converting enzyme inhibitor | Lisinopril | 1-80 mg/day |
| angiotensin converting enzyme inhibitor | Moexipril | 1-100 mg/day |
| angiotensin converting enzyme inhibitor | Enalapril | 2.5040 mg/day |
| angiotensin converting enzyme inhibitor | Benazepril | 10-80 mg/day |
| angiotensin II receptor antagonist | candesartan cilexetil | 2-32 mg/day |
| angiotensin II receptor antagonist | Inbesartan | |
| angiotensin II receptor antagonist | Losartan | 10-100 mg/day |
| angiotensin II receptor antagonist | Valsartan | 20-600 mg/day |
| calcium channel blocker | Verapamil | 100-600 mg/day |
| calcium channel blocker | Diltiazem | 150-500 mg/day |
| calcium channel blocker | Nifedipine | 1-200 mg/day |
| calcium channel blocker | Nimodipine | 5-500 mg/day |
| calcium channel blocker | Delodipine | |
| calcium channel blocker | Nicardipine | 1-20 mg/hr i.v.; 5-100 mg/day oral |
| calcium channel blocker | Isradipine | |
| calcium channel blocker | Amlodipine | 2-10 mg/day |
| diuretic | Hydrochlorothiazide | 5-100 mg/day |
| diuretic | Chlorothiazide | 250-2000 mg bid or tid |
| diuretic | Furosemide | 5-1000 mg/day |
| diuretic | Bumetanide | |
| diuretic | ethacrynic acid | 20-400 mg/day |
| diuretic | Amiloride | 1-20 mg/day |
| Diuretic | Triamterene | |
| Diuretic | Spironolactone | 5-1000 mg/day |
| Diuretic | Eplerenone | 10-150 mg/day |
| Vasodilator | Hydralazine | 5-300 mg/day |
| Vasodilator | Minoxidil | 1-100 mg/day |
| Vasodilator | Diazoxide | 1-3 mg/kg |
| Vasodilator | Nitroprusside | |

Additional calcium channel blockers which are useful in the combinations of the present invention include, without limitation, those shown in Table 5.

TABLE 5

| Compound Name | Reference |
|---|---|
| bepridil | U.S. Pat. No. 3,962,238 or U.S. Reissue No. 30,577 |
| clentiazem | U.S. Pat. No. 4,567,175 |
| diltiazem | U.S. Pat. No. 3,562,257 |
| fendiline | U.S. Pat. No. 3,262,977 |
| gallopamil | U.S. Pat. No. 3,261,859 |
| mibefradil | U.S. Pat. No. 4,808,605 |
| prenylamine | U.S. Pat. No. 3,152,173 |
| semotiadil | U.S. Pat. No. 4,786,635 |
| terodiline | U.S. Pat. No. 3,371,014 |
| verapamil | U.S. Pat. No. 3,261,859 |
| aranipine | U.S. Pat. No. 4,572,909 |
| bamidipine | U.S. Pat. No. 4,220,649 |
| benidipine | European Patent Application Publication No. 106,275 |
| cilnidipine | U.S. Pat. No. 4,672,068 |
| efonidipine | U.S. Pat. No. 4,885,284 |
| elgodipine | U.S. Pat. No. 4,962,592 |
| felodipine | U.S. Pat. No. 4,264,611 |
| isradipine | U.S. Pat. No. 4,466,972 |
| lacidipine | U.S. Pat. No. 4,801,599 |
| lercanidipine | U.S. Pat. No. 4,705,797 |
| manidipine | U.S. Pat. No. 4,892,875 |
| nicardipine | U.S. Pat. No. 3,985,758 |
| nifendipine | U.S. Pat. No. 3,485,847 |
| nilvadipine | U.S. Pat. No. 4,338,322 |
| nimodipine | U.S. Pat. No. 3,799,934 |
| nisoldipine | U.S. Pat. No. 4,154,839 |
| nitrendipine | U.S. Pat. No. 3,799,934 |
| cinnarizine | U.S. Pat. No. 2,882,271 |
| flunarizine | U.S. Pat. No. 3,773,939 |
| lidoflazine | U.S. Pat. No. 3,267,104 |
| lomerizine | U.S. Pat. No. 4,663,325 |
| Bencyclane | Hungarian Patent No. 151,865 |
| Etafenone | German Patent No. 1,265,758 |
| Perhexiline | British Patent No. 1,025,578 |

Additional ACE inhibitors which are useful in the combinations of the present invention include, without limitation, those shown in Table 6.

TABLE 6

| Compound Name | Reference |
|---|---|
| alacepril | U.S. Pat. No. 4,248,883 |
| benazepril | U.S. Pat. No. 4,410,520 |
| captopril | U.S. Pat. Nos. 4,046,889 and 4,105,776 |
| ceronapril | U.S. Pat. No. 4,452,790 |
| delapril | U.S. Pat. No. 4,385,051 |
| enalapril | U.S. Pat. No. 4,374,829 |
| fosinopril | U.S. Pat. No. 4,337,201 |
| imadapril | U.S. Pat. No. 4,508,727 |
| lisinopril | U.S. Pat. No. 4,555,502 |
| moveltopril | Belgian Patent No. 893,553 |
| perindopril | U.S. Pat. No. 4,508,729 |
| quinapril | U.S. Pat. No. 4,344,949 |
| ramipril | U.S. Pat. No. 4,587,258 |
| Spirapril | U.S. Pat. No. 4,470,972 |
| Temocapril | U.S. Pat. No. 4,699,905 |
| Trandolapril | U.S. Pat. No. 4,933,361 |

Additional beta adrenergic blockers which are useful in the combinations of the present invention include, without limitation, those shown in Table 7.

TABLE 7

| Compound Name | Reference |
|---|---|
| acebutolol | U.S. Pat. No. 3,857,952 |
| alprenolol | Netherlands Patent Application No. 6,605,692 |
| amosulalol | U.S. Pat. No. 4,217,305 |
| arotinolol | U.S. Pat. No. 3,932,400 |
| atenolol | U.S. Pat. No. 3,663,607 or U.S. Pat. No. 3,836,671 |
| befunolol | U.S. Pat. No. 3,853,923 |
| betaxolol | U.S. Pat. No. 4,252,984 |
| bevantolol | U.S. Pat. No. 3,857,981 |
| bisoprolol | U.S. Pat. No. 4,171,370 |
| bopindolol | U.S. Pat. No. 4,340,641 |
| bucumolol | U.S. Pat. No. 3,663,570 |
| bufetolol | U.S. Pat. No. 3,723,476 |
| bufuralol | U.S. Pat. No. 3,929,836 |
| bunitrolol | U.S. Pat. Nos. 3,940,489 and U.S. Pat. No. 3,961,071 |
| buprandolol | U.S. Pat. No. 3,309,406 |
| butiridine hydrochloride | French Patent No. 1,390,056 |
| butofilolol | U.S. Pat. No. 4,252,825 |
| carazolol | German Patent No. 2,240,599 |
| carteolol | U.S. Pat. No. 3,910,924 |
| carvedilol | U.S. Pat. No. 4,503,067 |
| celiprolol | U.S. Pat. No. 4,034,009 |
| cetamolol | U.S. Pat. No. 4,059,622 |
| cloranolol | German Patent No. 2,213,044 |
| dilevalol | Clifton et al., Journal of Medicinal Chemistry, 1982 25, 670 |
| epanolol | European Patent Publication Application No. 41,491 |
| indenolol | U.S. Pat. No. 4,045,482 |
| labetalol | U.S. Pat. No. 4,012,444 |
| levobunolol | U.S. Pat. No. 4,463,176 |
| mepindolol | Seeman et al., Helv. Chim. Acta, 1971, 54, 241 |
| metipranolol | Czechoslovakian Patent Application No. 128,471 |
| metoprolol | U.S. Pat. No. 3,873,600 |
| moprolol | U.S. Pat. No. 3,501,769 |
| nadolol | U.S. Pat. No. 3,935,267 |
| nadoxolol | U.S. Pat. No. 3,819,702 |
| nebivalol | U.S. Pat. No. 4,654,362 |
| nipradilol | U.S. Pat. No. 4,394,382 |
| oxprenolol | British Patent No. 1,077,603 |
| perbutolol | U.S. Pat. No. 3,551,493 |
| pindolol | Swiss Patent Nos. 469,002 and Swiss Patent Nos. 472,404 |
| practolol | U.S. Pat. No. 3,408,387 |
| pronethalol | British Patent No. 909,357 |
| propranolol | U.S. Pat. Nos. 3,337,628 and U.S. Pat. Nos. 3,520,919 |
| sotalol | Uloth et al., Journal of Medicinal Chemistry, 1966, 9, 88 |
| sufinalol | German Patent No. 2,728,641 |
| talindol | U.S. Pat. Nos. 3,935,259 and U.S. Pat. Nos. 4,038,313 |
| tertatolol | U.S. Pat. No. 3,960,891 |
| tilisolol | U.S. Pat. No. 4,129,565 |
| timolol | U.S. Pat. No. 3,655,663 |
| toliprolol | U.S. Pat. No. 3,432,545 |
| Xibenolol | U.S. Pat. No. 4,018,824 |

Additional alpha adrenergic blockers which are useful in the combinations of the present invention include, without limitation, those shown in Table 8.

TABLE 8

| Compound Name | Reference |
|---|---|
| amosulalol | U.S. Pat. No. 4,217,307 |
| arotinolol | U.S. Pat. No. 3,932,400 |
| dapiprazole | U.S. Pat. No. 4,252,721 |
| doxazosin | U.S. Pat. No. 4,188,390 |
| fenspirlde | U.S. Pat. No. 3,399,192 |

TABLE 8-continued

| Compound Name | Reference |
|---|---|
| indoramin | U.S. Pat. No. 3,527,761 |
| labetalol | U.S. Pat. No. 4,012,444 |
| naftopidil | U.S. Pat. No. 3,997,666 |
| nicergoline | U.S. Pat. No. 3,228,943 |
| prazosin | U.S. Pat. No. 3,511,836 |
| tamsulosin | U.S. Pat. No. 4,703,063 |
| Tolazoline | U.S. Pat. No. 2,161,938 |
| Trimazosin | U.S. Pat. No. 3,669,968 |
| Yohimbine | Raymond-Hamet, J. Pharm. Chim., 19, 209 (1934) |

Additional angiotensin II receptor antagonists, which are useful in the combinations of the present invention include, without limitation, those shown in Table 9.

TABLE 9

| Compound Name | Reference |
|---|---|
| Candesartan | U.S. Pat. No. 5,196,444 |
| Eprosartan | U.S. Pat. No. 5,185,351 |
| Irbesartan | U.S. Pat. No. 5,270,317 |
| Losartan | U.S. Pat. No. 5,138,069 |
| Valsartan | U.S. Pat. No. 5,399,578 |

Additional vasodilators which are useful in the combinations of the present invention include, without limitation, those shown in Table 10.

TABLE 10

| Compound Name | Reference |
|---|---|
| aluminum nicotinate | U.S. Pat. No. 2,970,082 |
| amotriphene | U.S. Pat. No. 3,010,965 |
| bamethan | Corrigan et al., Journal of the American Chemical Society, 1945, 67, 1894 |
| bencyclane | Hungarian Patent No. 151,865 |
| bendazol | J. Chem. Soc., 1968, 2426 |
| benfurodil hemisuccinate | U.S. Pat. No. 3,355,463 |
| benziodarone | U.S. Pat. No. 3,012,042 |
| betahistine | Walter et al., Journal of the American Chemical Society, 1941, 63, 2771 |
| bradykinin | Hamburg et al., Arch. Biochem. Biophys., 1958, 76, 252 |
| brovincamine | U.S. Pat. No. 4,146,643 |
| bufeniode | U.S. Pat. No. 3,542,870 |
| buflomedil | U.S. Pat. No. 3,895,030 |
| butalamine | U.S. Pat. No. 3,338,899 |
| cetiedil | French Patent No. 1,460,571 |
| chloracizine | British Patent No. 740,932 |
| chromonar | U.S. Pat. No. 3,282,938 |
| ciclonicate | German Patent No. 1,910,481 |
| cinepazide | Belgian Patent No. 730,345 |
| cinnarizine | U.S. Pat. No. 2,882,271 |
| citicoline | Kennedy et al., Journal of the American Chemical Society, 1955, 77, 250 or synthesized as disclosed in Kennedy, Journal of Biological Chemistry, 1956, 222, 185 |
| clobenfural | British Patent No. 1,160,925 |
| clonitrate | see Annalen, 1870, 155, 165 |
| cloricromen | U.S. Pat. No. 4,452,811 |
| cyclandelate | U.S. Pat. No. 2,707,193 |
| diisopropylamine dichloroacetate | Neutralization of dichloroacetic acid with diisopropyl amine |
| diisopropylamine dichloroacetate | British Patent No. 862,248 |
| dilazep | U.S. Pat. No. 3,532,685 |
| dipyridamole | British Patent No. 807,826 |
| droprenilamine | German Patent No. 2,521,113 |

TABLE 10-continued

| Compound Name | Reference |
|---|---|
| eburnamonine | Hermann et al., Journal of the American Chemical Society, 1979, 101, 1540 |
| efloxate | British Patent Nos. 803,372 and 824,547 |
| eledoisin | British Patent No. 984,810 |
| erythrityl | May be prepared by nitration of erythritol according to methods well-known to those skilled in the art. See e.g., Merck Index. |
| etafenone | German Patent No. 1,265,758 |
| fasudil | U.S. Pat. No. 4,678,783 |
| fendiline | U.S. Pat. No. 3,262,977 |
| fenoxedil | U.S. Pat. No. 3,818,021 or German Patent No. 1,964,712 |
| floredil | German Patent No. 2,020,464 |
| flunarizine | German Patent No. 1,929,330 or French Patent No. 2,014,487 |
| flunarizine | U.S. Pat. No. 3,773,939 |
| ganglefene | U.S.S.R. Patent No. 115,905 |
| hepronicate | U.S. Pat. No. 3,384,642 |
| hexestrol | U.S. Pat. No. 2,357,985 |
| hexobendine | U.S. Pat. No. 3,267,103 |
| ibudilast | U.S. Pat. No. 3,850,941 |
| ifenprodil | U.S. Pat. No. 3,509,164 |
| iloprost | U.S. Pat. No. 4,692,464 |
| inositol | Badgett et al., Journal of the American Chemical Society, 1947, 69, 2907 |
| isoxsuprine | U.S. Pat. No. 3,056,836 |
| itramin tosylate | Swedish Patent No. 168,308 |
| kallidin | Biochem. Biophys. Re&Commun., 1961, 6, 210 |
| kallikrein | German Patent No. 1,102,973 |
| khellin | Baxter et al., Journal of the Chemical Society, 1949, S 30 |
| lidoflazine | U.S. Pat. No. 3,267,104 |
| lomerizine | U.S. Pat. No. 4,663,325 |
| mannitol hexanitrate | May be prepared by the nitration of mannitol according to methods well-known to those skilled in the art |
| medibazine | U.S. Pat. No. 3,119,826 |
| moxisylyte | German Patent No. 905,738 |
| nafronyl | U.S. Pat. No. 3,334,096 |
| nicametate | Blicke & Jenner, J. Am. Chem. Soc., 64, 1722 (1942) |
| nicergoline | U.S. Pat. No. 3,228,943 |
| nicofuranose | Swiss Patent No. 366,523 |
| nimodipine | U.S. Pat. No. 3,799,934 |
| nitroglycerin | Sobrero, Ann., 64, 398 (1847) |
| nylidrin | U.S. Pat. Nos. 2,661,372 and 2,661,373 |
| papaverine | Goldberg, Chem. Prod. Chem. News, 1954, 17, 371 |
| pentaerythritol tetranitrate | U.S. Pat. No. 2,370,437 |
| pentifylline | German Patent No. 860,217 |
| pentoxifylline | U.S. Pat. No. 3,422,107 |
| pentrinitrol | German Patent No. 638,422-3 |
| perhexilline | British Patent No. 1,025,578 |
| pimefylline | U.S. Pat. No. 3,350,400 |
| piribedil | U.S. Pat. No. 3,299,067 |
| prenylamine | U.S. Pat. No. 3,152,173 |
| propatyl nitrate | French Patent No. 1,103,113 |
| prostaglandin El | May be prepared by any of the methods referenced in the Merck Index, Twelfth Edition, Budaved, Ed., New Jersey, 1996, p. 1353 |
| suloctidil | German Patent No. 2,334,404 |
| tinofedrine | U.S. Pat. No. 3,563,997 |
| tolazoline | U.S. Pat. No. 2,161,938 |
| trapidil | East German Patent No. 55,956 |
| tricromyl | U.S. Pat. No. 2,769,015 |
| trimetazidine | U.S. Pat. No. 3,262,852 |
| trolnitrate phosphate | French Patent No. 984,523 or German Patent No. 830,955 |
| vincamine | U.S. Pat. No. 3,770,724 |
| vinpocetine | U.S. Pat. No. 4,035,750 |

TABLE 10-continued

| Compound Name | Reference |
| --- | --- |
| Viquidil | U.S. Pat. No. 2,500,444 |
| Visnadine | U.S. Pat. Nos. 2,816,118 and 2,980,699 |
| xanthinol niacinate | German Patent No. 1,102,750 or Korbonits et al., Acta. Pharm. Hung., 1968, 38, 98 |

Additional diuretics which are useful in the combinations of the present invention include, without limitation, those shown in Table 11.

TABLE 11

| Compound Name | Reference |
| --- | --- |
| Acetazolamide | U.S. Pat. No. 2,980,676 |
| Althiazide | British Patent No. 902,658 |
| Amanozine | Austrian Patent No. 168,063 |
| Ambuside | U.S. Pat. No. 3,188,329 |
| Amiloride | Belgian Patent No. 639,386 |
| Arbutin | Tschb&habln, Annalen, 1930, 479, 303 |
| Azosemide | U.S. Pat. No. 3,665,002 |
| Bendroflumethiazide | U.S. Pat. No. 3,265,573 |
| Benzthiazide | McManus et al., 136th Am. Soc. Meeting (Atlantic City, September 1959). Abstract of Papers, pp 13-0 |
| benzylhydro-chlorothiazide | U.S. Pat. No. 3,108,097 |
| Bumetanide | U.S. Pat. No. 3,634,583 |
| Butazolamide | British Patent No. 769,757 |
| Buthiazide | British Patent Nos. 861,367 and 885,078 |
| Chloraminophenamide | U.S. Pat. Nos. 2,809,194, 2,965,655 and 2,965,656 |
| Chlorazanil | Austrian Patent No. 168,063 |
| Chlorothiazide | U.S. Pat. Nos. 2,809,194 and 2,937,169 |
| Chlorthalidone | U.S. Pat. No. 3,055,904 |
| Clofenamide | Olivier, Rec. Trav. Chim., 1918, 37, 307 |
| Clopamide | U.S. Pat. No. 3,459,756 |
| Clorexolone | U.S. Pat. No. 3,183,243 |
| Cyclopenthiazide | Belgian Patent No. 587,225 |
| Cyclothiazide | Whitehead et al., Journal of Organic Chemistry, 1961, 26, 2814 |
| Disulfamide | British Patent No. 851,287 |
| Epithiazide | U.S. Pat. No. 3,009,911 |
| ethacrynic acid | U.S. Pat. No. 3,255,241 |
| Ethiazide | British Patent No. 861,367 |
| Ethoxolamide | British Patent No. 795,174 |
| Etozolin | U.S. Pat. No. 3,072,653 |
| Fenquizone | U.S. Pat. No. 3,870,720 |
| Furosemide | U.S. Pat. No. 3,058,882 |
| Hydracarbazine | British Patent No. 856,409 |
| Hydrochlorothiazide | U.S. Pat. No. 3,164,588 |
| Hydroflumethiazide | U.S. Pat. No. 3,254,076 |
| Indapamide | U.S. Pat. No. 3,565,911 |
| Isosorbide | U.S. Pat. No. 3,160,641 |
| Mannitol | U.S. Pat. No. 2,642,462; or 2,749,371; or 2,759,024 |
| Mefruside | U.S. Pat. No. 3,356,692 |
| Methazolamide | U.S. Pat. No. 2,783,241 |
| Methyclothiazide | Close et al., Journal of the American Chemical Society, 1960, 82, 1132 |
| Meticrane | French Patent Nos. M2790 and 1,365,504 |
| Metochalcone | Freudenberg et al., Ber., 1957, 90, 957 |
| Metolazone | U.S. Pat. No. 3,360,518 |
| Muzolimine | U.S. Pat. No. 4,018,890 |
| Paraflutizide | Belgian Patent No. 620,829 |
| Perhexiline | British Patent No. 1,025,578 |
| Piretanide | U.S. Pat. No. 4,010,273 |
| Polythiazide | U.S. Pat. No. 3,009,911 |
| Quinethazone | U.S. Pat. No. 2,976,289 |
| Teclothiazide | Close et al., Journal of the American Chemical Society, 1960, 82, 1132 |

TABLE 11-continued

| Compound Name | Reference |
| --- | --- |
| Ticrynafen | U.S. Pat. No. 3,758,506 |
| Torasemide | U.S. Pat. No. 4,018,929 |
| Triamterene | U.S. Pat. No. 3,081,230 |
| Trichlormethiazide | deStevens et al., Experientia, 1960, 16, 113 |
| Tripamide | Japanese Patent No. 73 05,585 |
| Urea | Can be purchased from commercial sources |
| Xipamide | U.S. Pat. No. 3,567,777 |

The following Examples contain detailed descriptions of methods of preparation of the invention. These detailed descriptions are presented for illustrative purposes and not intended to limit or restrict the scope of the invention

EXAMPLES

Example 1

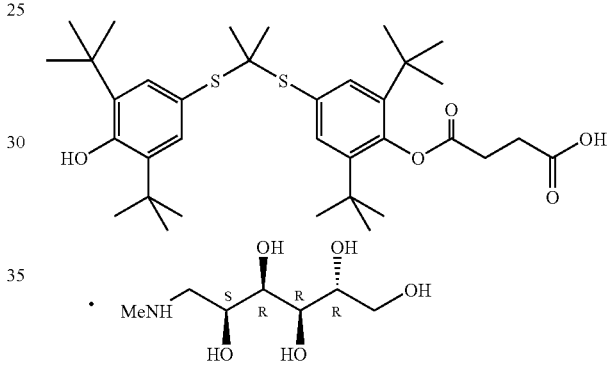

Butanedioic acid, mono [4-[[1-[[3,5-bis(1,1-dimethylethyl)-4-hydroxyphenyl]thio]-1-methylethyl]thio]-2,6-bis(1,1-dimethylethyl)phenyl]ester meglumine salt Meglumine (N-methyl-D-glucamine, 1.95 g, 10 mmol) was dissolved in water (4 mL). THF (8 mL) was added. An appropriate amount of methanol can be substituted for THF. Butanedioic acid, mono [4-[[1-[[3,5-bis(1,1-dimethylethyl)-4-hydroxyphenyl]thio]-1-methylethyl]thio]-2,6-bis(1,1-dimethylethyl)phenyl]ester (6.17 g, 10 mmol) was added followed by the addition of THF (20 mL). The resulting solution was stirred at room temperature for 30 minutes. The solution was evaporated. The residue was dissolved in THF (50 mL) and then evaporated. Crystallization from THF and hexane gave butanedioic acid, mono [4-[[1-[[3,5-bis(1,1-dimethylethyl)-4-hydroxyphenyl]thio]-1-methylethyl]thio]-2,6-bis(1,1-dimethylethyl)phenyl]ester meglumine salt as a white solid (7.30 g), m.p. 105-110° C. $^1$H NMR (300 MHz, CDCl$_3$) δ 7.60 (s, 2H), 7.42 (s, 2H), 5.5-6.05 (br. s, 5H), 5.38 (s, 1H), 4.14 (br. s, 1H), 3.62-3.85 (br. m, 5H), 3.08 (br. s, 2H), 2.92 (br. s, 2H), 2.50-2.61 (br. m, 5H), 1.42 (s, 6H), 1.40 (s, 18H), 1.27 (s, 18H). MS m/z=616 (M$^+$). Solubility in water: 0.39 mg/mL.

Example 2

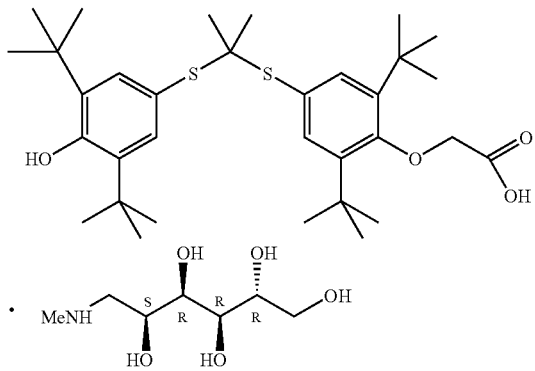

Acetic acid, [4-[[1-[[3,5-bis(1,1-dimethylethyl)-4-hydroxyphenyl]thio]-1-methylethyl]thio]-2,6-bis(1,1-dimethylethyl)phenoxy]-, meglumine salt Meglumine (N-methyl-D-glucamine, 1.95 g, 10 mmol) was dissolved in water (3 mL). THF (6 mL) was added. An appropriate amount of methanol can be substituted for THF. Acetic acid, [4-[[1-[[3,5-bis(1,1-dimethylethyl)-4-hydroxyphenyl]thio]-1-methyl-ethyl]thio]-2,6-bis(1,1-dimethylethyl)phenoxy]-(5.75 g, 10 mmol) was added followed by the addition of THF (14 mL). The resulting solution was stirred at room temperature for 30 minutes. It was evaporated and dried to give acetic acid, [4-[[1-[[3,5-bis(1,1-dimethylethyl)-4-hydroxyphenyl]thio]-1-methylethyl]thio] 2,6-bis(1,1-dimethylethyl)phenoxy]-, meglumine salt as a white solid (7.06 g), m.p. 71-76° C. $^1$H NMR (300 MHz, CDCl$_3$) δ 7.55 (s, 2H), 7.42 (s, 2H), 5.50-6.50 (br. s, 5H), 5.38 (s, 1H), 4.27 (br. s, 1H), 4.20 (br. S, 2H), 3.87 (br. S, 2H), 3.79 (br. S, 3H), 3.10-3.30 (br. m, 2H), 2.72 (br. s, 3H), 1.43 (s, 24H), 1.40 (s, 18H), 1.40 (s, 18H). MS m/z 574 (M$^+$). Solubility in water: 1.01 mg/mL.

Example 3

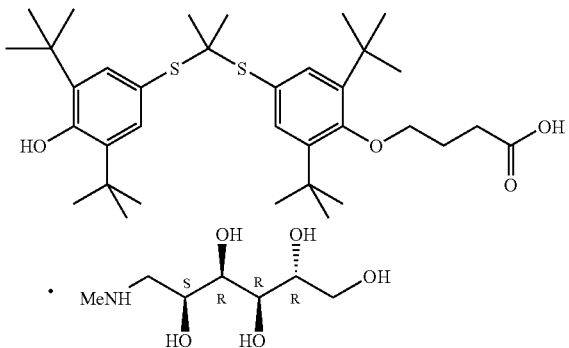

Butanoic acid, 4-[4-[[1-[[3,5-bis(1,1-dimethylethyl) 4-hydroxyphenyl]thio]-1-methylethyl]-thio]-2,6-bis (1,1-dimethylethyl)phenoxy]-, meglumine salt Meglumine (N-methyl-D-glucamine, 195 mg, 1 mmol) was dissolved in water (0.44 mL). THF (2 mL) was added. An appropriate amount of methanol can be substituted for THF. Butanoic acid, 4-[4-[[1-[[3,5-bis(1,1-dimethylethyl)4-hydroxyphenyl]thio]-1-methyl-ethyl]thio]-2,6-bis(1,1-dimethylethyl)phenoxy]-(603 mg, 1 mmol) was added followed by the addition of THF (4 mL). The resulting solution was stirred at room temperature for 30 minutes. The solution was evaporated. Crystallization from THF and hexane gave butanoic acid, 4-[4-[[1-[[3,5-bis(1,1-dimethylethyl)4-hydroxyphenyl]thio]-1-methylethyl]thio]-2,6-bis(1,1-dimethylethyl)phenoxy]-, meglumine salt as a white solid (504 mg), m.p. 124-126° C. $^1$H NMR (300 MHz, CDCl$_3$) δ 7.51 (s, 2H), 7.46 (s, 2H), 5.38 (s, 1H), 5.00-5.40 (br. s, 5H), 4.12 (br. s, 1H), 3.62-3.90 (br. m, 5H), 3.10 (br. s, 2H), 2.68 (br. s, 3H), 2.30 (br. s, 2H), 2.12 (br. s, 2H), 1.43 (s, 24H), 1.40 (s, 18H), 1.39 (s, 18H), 1.25 (t, 2H). MS m/z=602 (M$^+$). Solubility in water: 1.91 mg/mL.

Example 4

In Vitro VCAM-1 Assay

Cell Culture and compound dosing: Cultured primary human aortic (HAEC) or pulmonary (HPAEC) endothelial cells were obtained from Clonetics, Inc., and were used below passage 9. Cells were seeded in 96 well plates such that they would reach 90-95% confluency by the following day. On the following day the cells were stimulated with TNF-α (1 ng/ml) in the presence or absence of compounds dissolved in DMSO such that the final concentration of DMSO is 0.25% or less. To establish a dose curve for each compound, four concentrations in 2- to 5-fold increments were used. Cells were exposed to TNF-α and compounds for approximately 16 hours. The next day the cells were examined under microscope to score for visual signs of toxicity or cell stress.

Following 16 hr exposure to TNF-α and compound the media was discarded and the cells were washed once with Hanks Balanced Salt Solution (HBSS)/Phosphate buffered saline (PBS) (1:1). Primary antibodies against VCAM-1 (0.25 μg/ml in HBSS/PBS+5% FBS) were added and incubated for 30-60 minutes at 37° C. Cells were washed with HBSS/PBS three times, and secondary antibody Horse Radish Peroxidase (HRP)-conjugated goat anti-mouse IgG (1:500 in HBSS/PBS+5% FBS) were added and incubated for 30 minutes at 37° C. Cells were washed with HBSS/PBS four times and TMB substrate were added and incubated at room temperature in the dark until there was adequate development of blue color. The length of time of incubation was typically 5-15 minutes. 2N sulfuric acid was added to stop the color development and the data was collected by reading the absorbance on a BioRad ELISA plate reader at OD 450 nm. The results are expressed as IC$_{50}$ values (the concentration (micromolar) of compound required to inhibit 50% of the maximal response of the control sample stimulated by TNF-α only). IC$_{50}$'s of the Examples and the free acid of the Examples are tabulated in VCAM-1 Table 1a.

TABLE 1a

| Example No. | IC$_{50}$ (μM) (n = 3) | IC$_{50}$ (μM) of the free acid (n = 3) |
| --- | --- | --- |
| 1 | 13 | 7.7 |
| 2 | 6.5 | 10 |
| 3 | 12 | 11 |

Example 5

Solubility

Solubility of the Examples and of the free acid of the Examples are described in Table 2a.

TABLE 2a

| Example No. | (µg/ml) @ ~25° C. | Free acid (µg/ml) @ ~25° C. |
|---|---|---|
| 1 | 390 | <5 |
| 2 | 1010 | <5 |
| 3 | 1910 | <5 |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method for the treatment of rheumatoid arthritis, comprising administering to a host in need thereof a pharmaceutical composition comprising a compound of the formula:

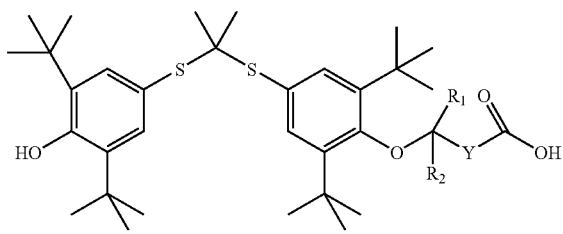

wherein:
$R_1$ and $R_2$ are independently hydrogen or alkyl or taken together to form a carbonyl; and
Y is $(CH_2)_{0-5}$; when $R_1$ and $R_2$ taken together form a carbonyl, Y is $(CH_2)_{1-5}$;
together with meglumine and a pharmaceutically acceptable carrier.

2. A method for the treatment of atherosclerosis, comprising administering to a host in need thereof a pharmaceutical composition comprising a compound of the formula:

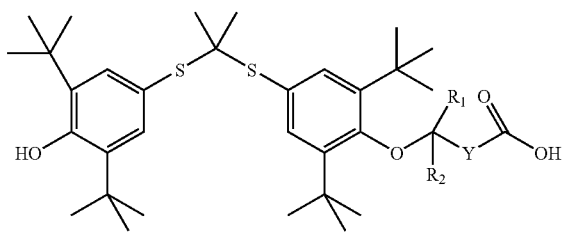

wherein:
$R_1$ and $R_2$ are independently hydrogen or alkyl or taken together to form a carbonyl; and
Y is $(CH_2)_{0-5}$; when $R_1$ and $R_2$ taken together form a carbonyl, Y is $(CH_2)_{1-5}$;
together with meglumine and a pharmaceutically acceptable carrier.

3. A method for treatment of hypercholesterolemia, comprising administering to a host in need thereof a pharmaceutical composition comprising a compound of the formula:

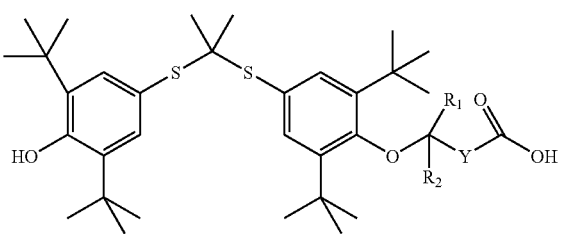

wherein:
$R_1$ and $R_2$ are independently hydrogen or alkyl or taken together to form a carbonyl; and
Y is $(CH_2)_{0-5}$; when $R_1$ and $R_2$ taken together form a carbonyl, Y is $(CH_2)_{1-5}$;
together with meglumine and a pharmaceutically acceptable carrier.

4. A method for treatment of hyperlipidemia, comprising administering to a host in need thereof a pharmaceutical composition comprising a compound of the formula:

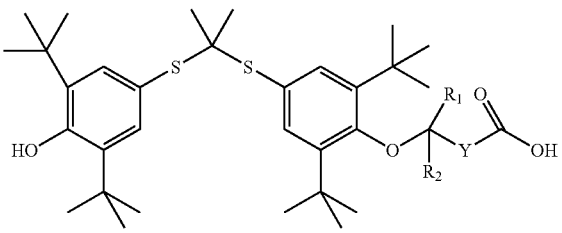

wherein:
$R_1$ and $R_2$ are independently hydrogen or alkyl or taken together to form a carbonyl; and
Y is $(CH_2)_{0-5}$; when $R_1$ and $R_2$ taken together form a carbonyl, Y is $(CH_2)_{1-5}$;
together with meglumine and a pharmaceutically acceptable carrier.

5. The method of claim 1, wherein $R_1$ and $R_2$ are taken together to form a carbonyl.

6. The method of claim 5, wherein Y is $(CH_2)_2$.

7. The method of claim 1, wherein $R_1$ and $R_2$ are each hydrogen.

8. The method of claim 7, wherein Y is $(CH_2)_0$.

9. The method of claim 7, wherein Y is $(CH_2)_2$.

10. The method of claim 2, wherein $R_1$ and $R_2$ are taken together to form a carbonyl.

11. The method of claim 10, wherein Y is $(CH_2)_2$.

12. The method of claim 2, wherein $R_1$ and $R_2$ are each hydrogen.

13. The method of claim 12, wherein Y is $(CH_2)_0$.

14. The method of claim 12, wherein Y is $(CH_2)_2$.

15. The method of claim 3, wherein $R_1$ and $R_2$ are taken together to form a carbonyl.

16. The method of claim 15, wherein Y is $(CH_2)_2$.

17. The method of claim 3, wherein $R_1$ and $R_2$ are each hydrogen.

18. The method of claim 17, wherein Y is $(CH_2)_0$.

19. The method of claim 17, wherein Y is $(CH_2)_2$.

20. The method of claim 4, wherein $R_1$ and $R_2$ are taken together to form a carbonyl.

21. The method of claim 20, wherein Y is $(CH_2)_2$.

22. The method of claim 4, wherein $R_1$ and $R_2$ are each hydrogen.

23. The method of claim 22, wherein Y is $(CH_2)_0$.

24. The method of claim 22, wherein Y is $(CH_2)_2$.

* * * * *